United States Patent
Jacobson

(10) Patent No.: US 9,414,893 B2
(45) Date of Patent: Aug. 16, 2016

(54) PROTECTIVE BOX FOR SURGERY

(71) Applicant: Daniel R. Jacobson, Chicago, IL (US)

(72) Inventor: Daniel R. Jacobson, Chicago, IL (US)

(\*) Notice: Subject to any disclaimer, the term of this patent is extended or adjusted under 35 U.S.C. 154(b) by 56 days.

(21) Appl. No.: 14/287,668

(22) Filed: May 27, 2014

(65) Prior Publication Data
US 2014/0346072 A1    Nov. 27, 2014

Related U.S. Application Data
(60) Provisional application No. 61/827,508, filed on May 24, 2013, provisional application No. 61/836,806, filed on Jun. 19, 2013.

(51) Int. Cl.
*A61B 50/31* (2016.01)

(52) U.S. Cl.
CPC ............... *A61B 50/31* (2016.02); *A61B 50/30* (2016.02); *A61B 50/33* (2016.02); *A61B 2050/0056* (2016.02); *A61B 2050/0067* (2016.02); *A61B 2050/0074* (2016.02); *A61B 2050/3006* (2016.02); *A61B 2050/3008* (2016.02); *A61B 2050/3011* (2016.02); *A61B 2050/3015* (2016.02); *A61B 2050/311* (2016.02)

(58) Field of Classification Search
CPC ............. A61B 50/31; A61B 2050/005; A61B 2050/3006; A61B 2050/3015; A61B 2050/311
USPC ............................... 53/449, 425; 606/102, 133
See application file for complete search history.

(56) References Cited

U.S. PATENT DOCUMENTS

| | | | | |
|---|---|---|---|---|
| 3,366,230 | A | * | 1/1968 | Loran ................. A61C 5/02 206/63.5 |
| 3,726,057 | A | * | 4/1973 | Kemble ........... A61B 17/06133 422/40 |
| 3,728,839 | A | * | 4/1973 | Glick ............... A61B 17/06133 206/210 |
| 4,065,816 | A | * | 1/1978 | Sawyer ................ A61F 2/2427 206/438 |
| 4,068,655 | A | * | 1/1978 | LeRoy .................. A61B 17/02 128/852 |
| 4,373,629 | A | * | 2/1983 | Ulin ....................... A45C 11/24 206/350 |
| 4,603,538 | A | * | 8/1986 | Shave ............. A61B 17/06133 53/425 |
| 4,671,943 | A | * | 6/1987 | Wahlquist ................ A61L 2/26 206/363 |
| 4,754,595 | A | * | 7/1988 | Sanderson ............... A61L 2/26 53/425 |
| 4,777,780 | A | * | 10/1988 | Holzwarth ............ B65D 81/268 53/432 |
| 4,813,210 | A | * | 3/1989 | Masuda .................. A61L 2/26 206/210 |
| 4,828,113 | A | * | 5/1989 | Friedland ............... A61C 19/02 206/369 |
| 4,878,486 | A | * | 11/1989 | Slater ..................... A61B 1/267 206/438 |

(Continued)

*Primary Examiner* — Gloria R Weeks
(74) *Attorney, Agent, or Firm* — BrainSpark Associates, LLC

(57) ABSTRACT

The present invention is directed to providing a sterile container protecting various surgical grafts, implants and devices from incidental contamination and damage during operative procedures. The design includes an inner box to contain the items, and an outer box to protect the exterior of the inner box from contamination in the event of fall or other contamination, such as from airborne particles or liquids, fall from the sterile field, or by non-sterile handling. In the event of fall or contamination of the outer box, the surgical staff will be able to recover the inner box and its contents in sterile and unspoiled condition without difficulty.

18 Claims, 25 Drawing Sheets

(56) References Cited

U.S. PATENT DOCUMENTS

| | | | | |
|---|---|---|---|---|
| 4,886,165 | A * | 12/1989 | Annett | A61B 50/31 206/350 |
| 4,932,552 | A * | 6/1990 | Wilson | A61B 19/0271 206/229 |
| 5,098,676 | A * | 3/1992 | Brooks, Jr. | A61L 2/26 206/438 |
| 5,144,942 | A * | 9/1992 | Decarie | A61B 1/00144 206/363 |
| 5,350,060 | A * | 9/1994 | Alpern | A61B 17/06133 206/380 |
| 5,390,792 | A * | 2/1995 | Van Ness | A61L 2/26 206/213.1 |
| 5,392,918 | A * | 2/1995 | Harrison | A61M 25/002 206/364 |
| 5,441,707 | A * | 8/1995 | Lewis | A61L 2/26 206/438 |
| 5,600,395 | A * | 2/1997 | Balling | G03B 17/30 396/513 |
| 5,607,612 | A * | 3/1997 | Held | A61L 2/12 219/728 |
| 5,628,970 | A * | 5/1997 | Basile | A61L 2/26 206/363 |
| 5,645,748 | A * | 7/1997 | Schiffmann | A61L 2/12 219/710 |
| 5,759,502 | A * | 6/1998 | Spencer | A61L 2/26 206/370 |
| 5,842,326 | A * | 12/1998 | Wolf | A61L 2/07 422/25 |
| 6,029,422 | A * | 2/2000 | Alt | 53/425 |
| 6,412,639 | B1 * | 7/2002 | Hickey | 206/438 |
| 6,594,971 | B1 * | 7/2003 | Addy | A61B 1/00142 53/413 |
| 7,036,661 | B2 * | 5/2006 | Anthony | 206/363 |
| 7,100,768 | B2 * | 9/2006 | Grimard | A61L 2/183 206/438 |
| 7,694,814 | B1 * | 4/2010 | Cristobal | A61B 8/00 206/438 |
| 7,712,606 | B2 * | 5/2010 | Salahieh | A61F 2/0095 206/210 |
| 7,909,191 | B2 * | 3/2011 | Baker | A61L 2/26 220/23.4 |
| 7,942,264 | B2 * | 5/2011 | Friderich | A61L 2/26 206/370 |
| 7,993,602 | B2 * | 8/2011 | Moriyama | A61B 1/123 400/300 |
| 8,226,669 | B2 * | 7/2012 | Detruit | A61F 2/0095 206/363 |
| 8,241,587 | B2 * | 8/2012 | Friderich | A61L 2/26 206/439 |
| 2007/0095699 | A1 * | 5/2007 | Frieze | A61L 2/07 206/438 |
| 2012/0305427 | A1 * | 12/2012 | Felder | A61M 5/002 206/438 |
| 2012/0325704 | A1 * | 12/2012 | Kerns | A61B 19/0271 206/370 |
| 2013/0009606 | A1 * | 1/2013 | Smith | A61B 50/20 320/137 |

\* cited by examiner

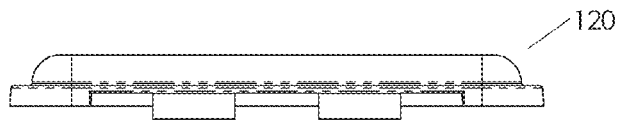
FIG. 29
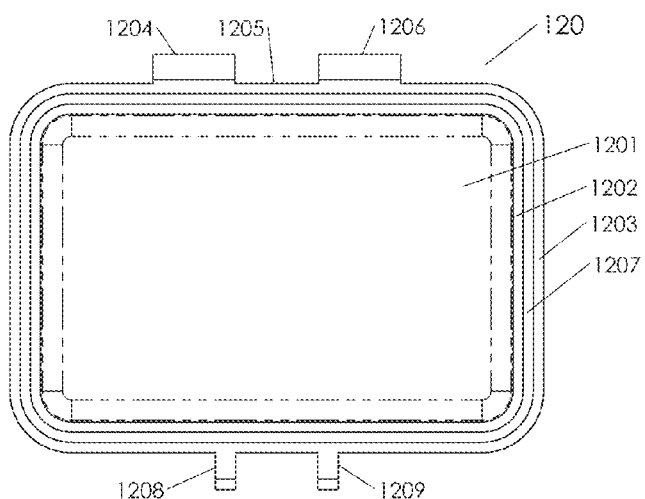
FIG. 30
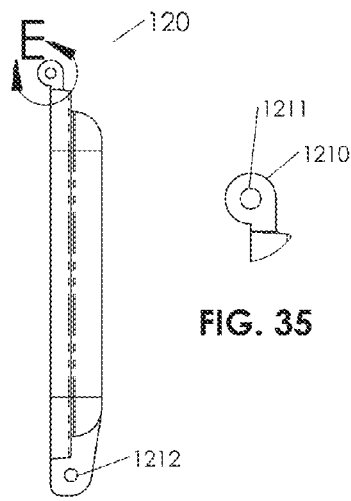
FIG. 31
FIG. 35
FIG. 32
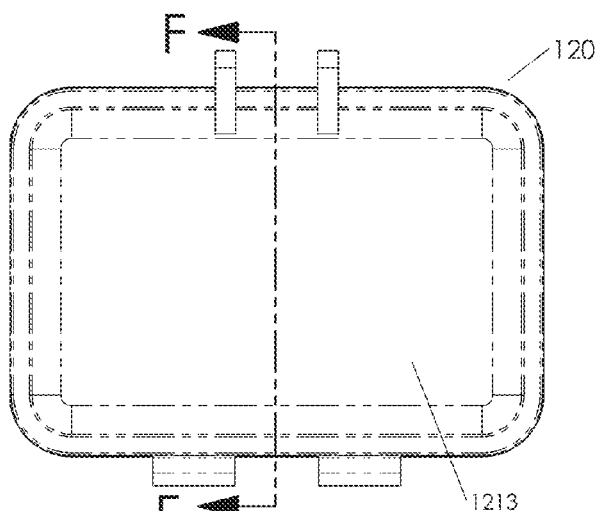
FIG. 33
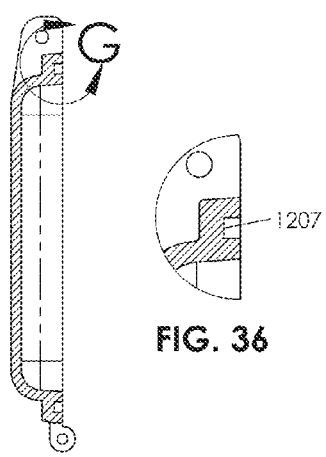
FIG. 34
FIG. 36

FIG. 54
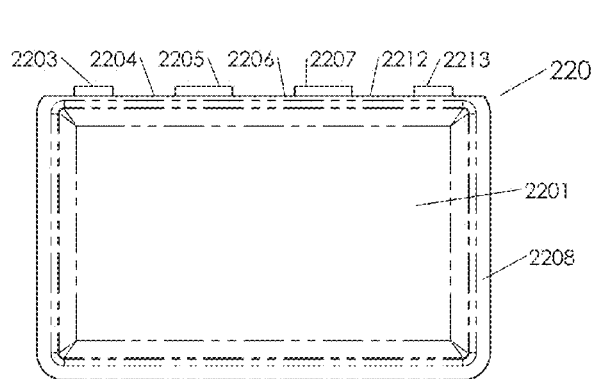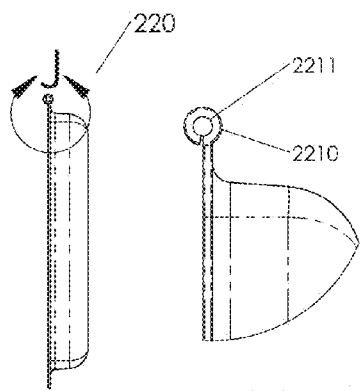
FIG. 55   FIG. 56   FIG. 60
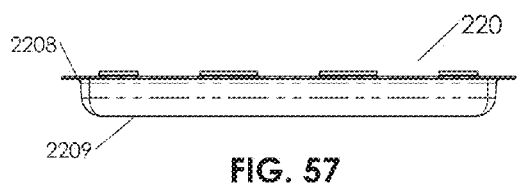
FIG. 57
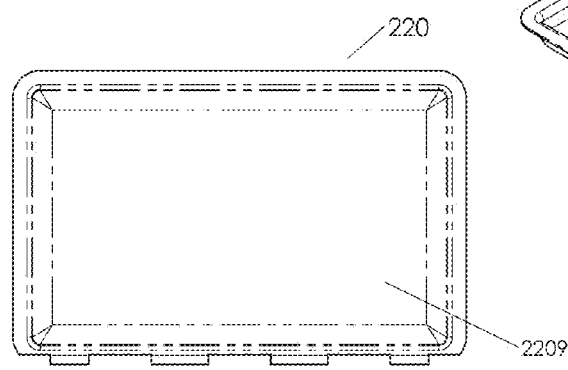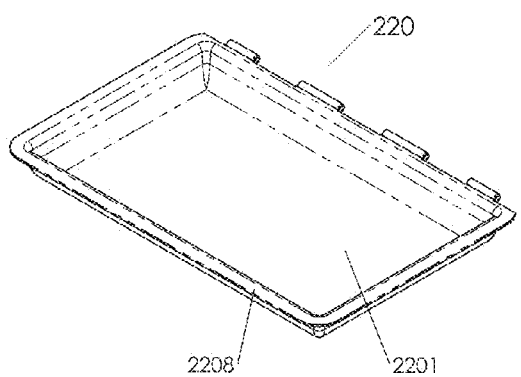
FIG. 58   FIG. 59

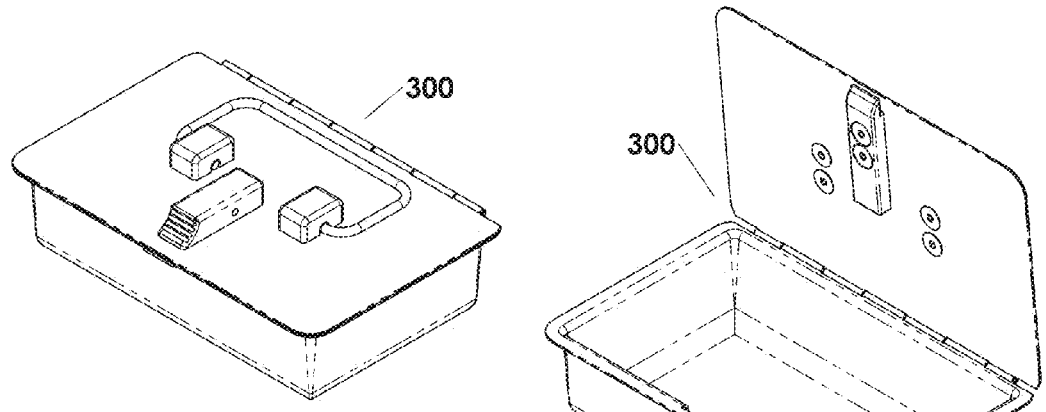
FIG. 61
FIG. 62
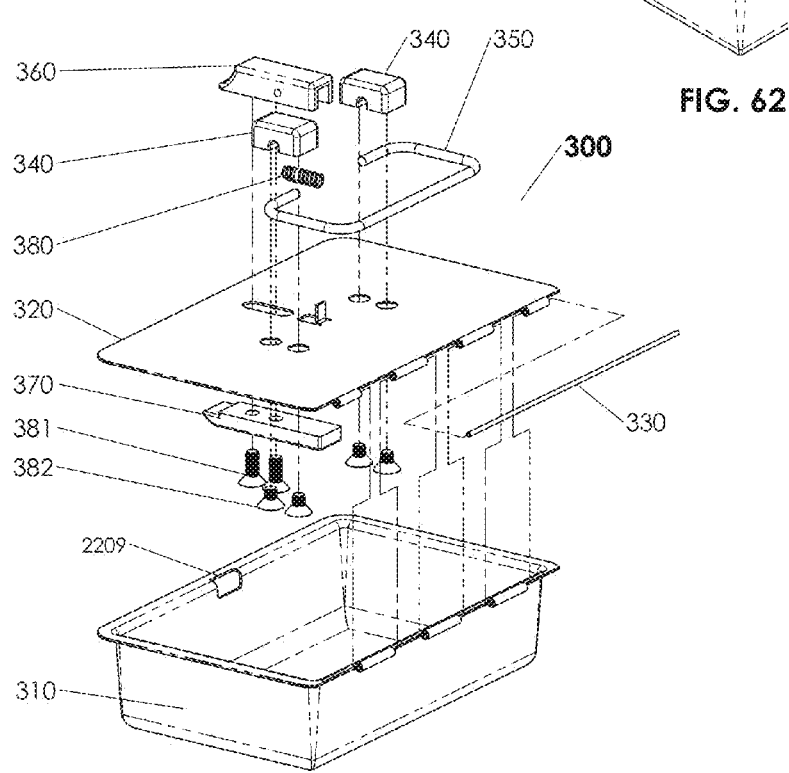
FIG. 63

PROTECTIVE BOX FOR SURGERY

CROSS-REFERENCE TO RELATED APPLICATIONS

This application claims priority from U.S. Provisional Patent Application No. 61/827,508 filed May 24, 2013, entitled "Protective Box for Surgery" and U.S. Provisional Patent Application No. 61/836,806, filed Jun. 19, 2013, entitled "Protective Box for Surgery," the contents of which both are hereby incorporated herein by reference in their entireties.

FIELD OF THE INVENTION

The invention relates to improved methods, systems, tools and protective enclosures used in various applications to prevent the contamination of specimens, products and components. More specifically, the invention relates to improved tools used in the field of surgery to transport, store, prepare and prevent the contamination of biologic specimens.

BACKGROUND OF THE INVENTION

The current practice of surgery often requires the use of implantable materials including various grafts, implants, and devices. Examples of these applications can include the surgical implantation of natural, biologic, synthetic and/or artificial materials, such as autografts, allografts, and xenografts (such as bone, vein, skin, kidneys, livers, hearts, and other cells, tissues and organs); expensive synthetic and biologic implants and prostheses; and electronic devices such as pacemakers, stimulators, artificial organs, ventricular assist devices and pumps. In many cases, the graft tissues harvested from the surgical patient or other donors, as well as implants and other medical devices, can be invaluable to the success of the surgical operation. In many cases, the unique properties of donated tissues, as well as the exorbitant expense of many implants and medical device, can obviate the availability of "replacements" if the tissues, implants or devices are contaminated or otherwise damaged or compromised during the course of an operation. Death or serious complications can result from contamination to, or loss of, available transplant organs and tissues, implants, or medical devices because of contamination or damage. Some implants can cost over $80,000 USD, and contamination of these grafts and/or devices typically renders them non-usable and would require opening a new item, assuming a replacement is immediately available. Moreover, there is often a significant delay between the time a graft is harvested or an item which must maintain sterility is opened onto the sterile surgical field and its use or implantation during the surgical procedure. The longer the delay, the more chances there are for contamination or damage.

SUMMARY OF THE INVENTION

The invention includes the realization of a need for a protective enclosure and/or environment for surgical tissue grafts, implants and/or other biologics/devices prior to and during a surgical procedure, where the material is readily available for the surgeon's use, but which protects the material from inadvertent contamination and/or damage from a variety of potential causes. Various embodiments described herein relate generally to the field of surgery and/or material storage and/or transport, and can be used in various applications, such as the protection of laboratory specimens (DNA, microorganism cultures, cell lines), forensic evidence for chain of evidence (sexual assault evidence collection kits), biologic materials (protein rich plasma, blood and blood products), cells for implant (bone marrow transplants, stem cells), chemotherapy agents, injectable drugs, and devices for human or animal implantation. Alternatively, other potential uses may include applications for biologic, medical, and warfare research, and protection of industrial products and components. In one exemplary embodiment, the invention incorporates a reusable or disposable "box within a box" design (i.e., nested boxes) for storage and protection of surgical "materials," such that in the event the entire box is knocked to the floor or otherwise contaminated in some manner, the interior and exterior of the nested inner box will remain sterile even when the outer box contacts the floor of the operating room, other non-sterile equipment/personnel, or otherwise becomes contaminated. If contamination to the outer box occurs, the outer box can be opened by non-sterile operating room personnel, and the sterile personnel within the sterile field can lift the inner box and/or its contents from the outer box and directly return the inner box/material to the sterile surgical field with no fear of contamination or damage to the material.

In various embodiments, the protective box can isolate expensive and often irreplaceable surgical materials from contamination and/or damage during the period between harvesting or opening and implantation. If desired, the box may incorporate features that facilitate the removal of sterile contents from a first surgical field, such as where organs have been harvested for transplantation, allowing transport of the organ to a second sterile location, and the box can subsequently be opened in a sterile condition into the second surgical field. This arrangement can prevent the significant cost and potential catastrophic complications of contamination, damage and/or loss of the box contents. If desired, the inner box (which desirably remains sterile) can be removed from a first outer enclosure (which would typically become contaminated during transport) and placed into a second outer enclosure (which could be sterile, if desired), and the sterile "box within a box" subsequently brought into the sterile field of the operating room.

In various embodiments, the design may also incorporate various automated and/or mechanical closure and/or locking mechanisms to desirably close, seal and/or prevent opening of the inner and/or outer box portions during various stages of the operation and/or during a fall to the floor of the operating room.

In various alternative embodiments, the protective enclosure may incorporate a single box design that can be constructed to be strong, sterilizable, sealed, locked, and/or lined, with features to desirably prevent contamination and/or damage to the box contents in the event of a fall or non-sterile handling. A single box design may be used in a variety of ways, such as to allow surgical staff to remove the box contents to be positioned onto the surgical field, removing box contents for placement onto a table or into a separate protective box or other suitable sterile container, and/or the contents of the box may be preassembled, manufactured, and/or placed inside the single box prior to sterilization and shipping to the desired destination (typically in the case of implants and/or surgical tools). In various embodiments, a manufacturer may incorporate some or all of the relevant features described herein in a commercial nested box design and/or a single box design, such that the device will desirably assist with the prevention of contamination and/or shock damage. In various embodiments, a single box design might be manufactured less expensively that a corresponding nested box design, primarily due to the reduction of the number of component parts, and an exemplary single box design might include any variety of the features (and/or combinations of features) as described in conjunction with the inner and/or outer nested boxes herein. If desired, a single box design might incorporate an auxiliary storage enclosure within the box, such as a plastic or metallic bag or other flexible and/or non-rigid secondary enclosure, which could desirably maintain sterility and/or prevent contamination of the enclosed contents in the event of damage to the single box (in a manner similar to the "nested box" designs described herein). Alternatively, the single box design could include an inner "lid" (mounted internally within the box) that seals an internal portion of the box from the surrounding environment, while an external "lid" seals the entire internals of the box. This "lid within a lid" design might also be useful to secure materials from contamination in a manner similar to the "nested box" designs described herein, although with varying degrees of utility for the surgeon and operating room personnel.

In various embodiments, the outer and/or inner box and/or single box lid may contain a seal to ensure a waterproof and/or a dustproof construct. Alternatively, the outer and/or inner box and/or single lid may be designed with a magnetic or other self-closing seal. The inner and/or outer and/or single box lid may incorporate a built in or connected/removable magnifying lens and/or include a clear top to the boxes so that the surgeon and staff can see into the box contents without opening. Desirably, there may be a ruler or other measuring tools built into the inner and/or outer and/or single box lid for convenient in-field measurements of grafts and implants. Furthermore, the inner and/or outer and/or single box lid may also incorporate features of various shapes and sizes, and protective liners and casings, to accommodate the tissue, drug, device, and/or component. The lid may be flat, recessed, concave, convex, dome shaped, trapezoidal shaped, custom shaped, or any combination thereof.

In other exemplary embodiments, there may be incorporated various combinations of cutouts, depressions, or recesses on the inner or single box lid to hold certain surgical instruments (clamps, cannulas, tools) required for preparation of the protected items. There may be fixed, adjustable and/or removable dividers to separate and organize the box contents, and these dividers may be formed from rigid or flexible materials, as well as shock-absorbing and/or water permeable materials, if desired. The dividers may also be designed to render compartments watertight, or prevent cross-contamination between compartments. There may be a hole or hasp in the latch or body of the outer or single box to accommodate a tamperproof or tamper evident seal. Various features can be provided within the box to allow customization of the various compartmental dividers by the user, if desired.

In other embodiments, a cushioned liner or shock absorbing material can be placed between the inner and outer boxes, or placed within the cavity of the inner and/or outer and/or single boxes to protect sensitive implants and/or specimens. Also, it may be advantageous to have the inner box designed with a plurality of holes or other features to drain any excess fluids into the cavity of the outer box. Furthermore, the box components may be available in multiple standard sizes and/or shapes of the protective box inner and/or outer and/or single boxes, and/or custom boxes to accommodate different items. Larger designs could be used for organs or larger tissue samples or grafts. Smaller dimensions could be more appropriate for tissue grafts and implants, as well as to desirably occupy limited space in the sterile surgical field. Dimensions and shapes may vary by the size and shape of the protected items, or it may be advantageous to integrate standard and custom shapes and sizes for the inner, outer, and/or single box, especially to accommodate specific implantable devices. If desired, multiple inner boxes may be contained within a single outer box.

In various embodiments, the outer and/or inner box and/or single box bottom container may include various securing features for securing the container to the surrounding sterile environment, such as to a surgical tray and/or table. The securing features may be fixed/integrated and/or removable. The inner and outer and single box may be designed with a skid resistant bottom (i.e., rubber or textured material), with or without magnetic components, hook and loop mechanisms and/or strap supports to allow the box to be adhered or otherwise "linked" to a tray or table and desirably reduce the risk the box falling from the instrument table if it is inadvertently contacted or moved prior to and/or during the surgical procedure.

In various other embodiments, the various "nested" boxes and/or single boxes may be designed as reusable, disposable, and/or "resposable" (i.e., the boxes can be re-tasked and/or re-used for other uses, which may include non-surgical uses). If the boxes are designed as reusable boxes, they may be made of sterilizable materials and sterilized by autoclaving or gas sterilization while in an open position, and/or any optimal method that is available on the clinical site. Various components of the boxes may be disassembled (i.e., removable lids, etc.) to facilitate such cleaning and/or sterilization.

Reusable nested or single boxes may reduce the overall cost for procedures done frequently, as resterilization is typically less expensive than using a new disposable box, but may offer fewer customized design capabilities. However, cleaning and resterilization could be time consuming and costly, which may render a disposable design (for some or all of the box components) more desirable. If the nested boxes or single boxes are designed as disposable boxes, they may be made of impact and/or damage resistant, surgical grade materials. Disposable boxes often offer the advantage of having a new seal and clear top for each use (i.e., they are not clouded or otherwise scratched during repeated sterilization procedures), and they generally do not need to be fixed and/or maintained between surgical procedures. Disposable surgical devices are frequently cost competitive with reusable counterparts, and may be more profitable for a manufacturer. It may be desirous to match a disposable inner box with a reusable outer box, or any combination thereof, especially where the inner box may be formed from a less-durable material than the outer box. Because of certain infectious considerations, items in contact with brain or spinal tissues, such as cranial bone flaps, often should not or cannot be reused. A disposable box might be more appropriate for use with such tissues during neurosurgical or other procedures.

The nested or single boxes may also be manufactured as "resposable." The nested or single box designs may be optionally disposable and/or one or more other components within the nested and/or single box being reusable. Alternatively, the one or more components may be optionally disposable, and/or the nested and/or single box may be reusable. Resposable boxes may desirably provide some advantages, such as allowing reuse of at least a portion of the components, nested boxes or single boxes, they may be manufactured using high strength materials, and they can be sterilizable, but when damaged or worn they can be disposed of relatively inexpensively.

In other embodiments, the single and/or nested inner and outer boxes may be designed to incorporate various colors. The colors may indicate the specific application for the boxes. For example, there may be color coding for the protection of laboratory specimens (DNA, microorganism cultures, cell lines), forensic evidence for chain of evidence (sexual assault evidence collection kits), biologic materials (protein rich plasma, blood and blood products), cells for implant (bone marrow transplants, stem cells), chemotherapy agents, injectable drugs, and devices for human or animal implantation. In addition, color-coding or similar identification features and/or schemes may also apply to other uses, such as applications for biologic and medical and warfare research, the protection of industrial products and components, and any combination of applications discussed above.

In a preferred embodiment, one exemplary method of use for surgery may desire the single or nested boxes to be sterilized by customary techniques and possibly stored in a sterile peel pack until ready for use. The surgeon and/or staff may open one or more boxes in a standard pre-operative or operative fashion, and place the boxes onto the surgical instrument table using sterile technique. The surgical staff may desire additional security for the boxes on the surgical instrument table (i.e., to prevent and/or reduce unnecessary movement). Increased stability of the boxes on the table may include the use of peelable adhesive tape or backing on the box that sticks to a surgical table (which may desirably may include or require removal of some backing to activate various adhesive features of the box), or hook and loop mechanism, or the box may include magnetic features to facilitate adhesion of the box to a surgical steel table or sterile magnet, and/or may require adding various features that may help with securing the outer box to the surgical instrument table. The inner box may be placed in the outer box. Items can be placed within the inner box. Both boxes can then be opened and/or closed at various times during the surgical procedure, but desirably the combined box will remain closed when not immediately being used. In the event of contamination to the outer box (i.e., blood or other fluid spatter from non-sterile equipment), or the transportation of the contained materials to a different surgical room or other location is desired, and/or otherwise passing of the box through a non-sterile environment is desired (which may resulting in rendering the outer box non-sterile in some manner), the operating room nurse, who is typically away from the surgical field (and thus is often allowed to handle "non-sterile" items) can open the outer box in such a way that the inner box does not get touched. The surgical technician, or surgeon, who is gowned and gloved sterily, can then lift the handle of the inner box and place it on the sterile surgical instrument table without touching the exterior of the outer box. Alternatively, the surgeon or technician may desirably use a tool to grab the handle of the inner box to place it on the sterile surgical table. The inner box and/or single box may include a non-skid bottom, an adhesive bottom with a removable backing, a magnetic bottom, and/or any other feature to secure the inner box or single box to the surgical table. This method desirably preserves the sterile integrity of the box contents, as well as allows the surgeon to place and access the box within the sterile field. The contaminated outer box can be re-sterilized ("flashed") if reusable, or a separate disposable box (nested or single box) can be opened to again prevent contamination of the recovered inner box.

The use of such "nested" or "single" boxes of the present design allows the sterile contents to be protected while allowing the single or outer box to be easily manipulated in various environments, including by use of non-sterile procedures. Such use could include storage of the box in a standard refrigerator or freezer, transport via common carrier and/or via post, and/or transporting the box in a cooler filled with non-sterile ice or other cooling medium. Once access to the contents is desired, the single box may be opened and/or the outer box may be opened with the sterile inner box removed, and the contents and/or the inner box may be directly placed into the sterile surgical field for use during the surgical procedure.

In various additional embodiments, certain tissues, surgical implants and biologics may be packaged sterily in a custom sized and lined protective single or nested box design such that the implants are protected from contamination and/or shock damage from the moment they are sterilized at the manufacturing plant or sterilizing facility until they are opened on the surgical field. This process will desirably protect the implants from damage and contamination during storage, transport, and handling. Using the protective box in this manner will add value to the implant as the integrity of the implant is assured, especially when comparing to a competitor's implant that does not use a similar protective box arrangement. Furthermore, the surgical team may be able to employ the advantages imparted by the protective box at little or no additional cost, adding further comparative value to the manufacturer's product and service. In at least one exemplary embodiment, the inner box could contain an implant sterilized using a variety of technologies, including the use of materials such as Ethylene-Oxide (EtO) sterilization gas.

In yet another preferred embodiment, the single or nested box design may have a section or compartment specifically designed to fit and/or line a custom sized implant or specimen and another compartment for other grafts, implants, and biologics. This could potentially create a competitive advantage for the manufacturer's products, as the supplier of the customized box with the manufactured implant can also supply one or more auxiliary compartments within the box for the surgeon's use during the surgical procedure, providing a convenient and compact storage solution for all surgical materials and making the entire system more desirable and/or "user friendly" to the surgeon.

In another exemplary embodiment, the manufacturer may incorporate various other features into the design of a single or nested box, such as for multiple uses after the intended single use of the single and/or nested box. Exemplary designs could include features that facilitate secondary cleaning, sterilization and/or other decontamination procedures to be performed on the box and/or its component parts to allow a third party to reuse or recycle the box designs for completely different applications. For example, the shape and dimensions of popular consumer electronics, such as cell phones, cameras, music players, tablets, and glasses, or for items used in outdoor environments such as first-aid kits, flashlights, and matches, may "match" (to various degrees) the shape and/or dimensions of an inner and/or outer protective box design (such as the various designs described herein). The protective box manufacturer may design the protective box components so as to facilitate storage and/or protection of such third-party devices (after initial use in the surgical procedure), thereby allowing a consumer to use the single or nested box for placement and fit of these consumer products within the box designs and/or box components. This feature will desirably keep the "used" boxes out of the waste stream, and can potentially provide a marketing and/or sales benefit as the original customers can keep the recycled box for their own use.

In another alternative embodiment, the nested or single box design may include a variety of lighting features within the box. The lighting may be provided for more convenient viewing and/or may incorporate a manual switch and/or automatic switch when open or closed. The lighting may also allow intensity adjustment or may be moved multi-directionally within the box designs to allow discreet or specific lighting to a selected area of the boxed contents. Also, the lighting may be integrated within the box designs or provided as a modular system. Lighting system may include powered systems (i.e., using LED bulbs and stored battery power) or may utilize "natural lighting" features such as lens collection and/or transmission (i.e., "piping" of light using optical fibers) of ambient light from the operating room environment into the box.

BRIEF DESCRIPTION OF THE DRAWINGS

Various preferred embodiments of the invention are described herein in detail with references to the accompanying drawings, wherein reference numerals refer to the corresponding elements in the drawings.

FIGS. 29-33 depict various exemplary views of one embodiment of an outer box lid;

FIG. 34 depicts a cross-sectional side view of the outer box lid of FIG. 33, taken along line F-F;

FIG. 35 depicts a magnified view of the hinge aperture of the outer box lid of FIG. 31;

FIG. 36 depicts a magnified view of the O-ring channel of the outer box lid along view G of FIG. 34;

FIGS. 54-59 depict various exemplary views of one embodiment of an inner box lid;

FIG. 60 depict a magnified view of the hinge aperture of the inner box lid of FIG. 56, taken along line J;

FIGS. 61-62 depict isometric views of an alternative embodiment of an inner box with a handle locking mechanism in an open and closed position;

FIG. 63 depicts an exploded isometric view of the inner box with a handle locking mechanism of FIG. 61;

DETAILED DESCRIPTION

The drawings and the following description relate to preferred embodiments by way of illustration only. It should be noted that from the following description, alternative embodiments of the components and methods disclosed herein will be readily recognizable as viable alternatives that may be employed in one skilled in the art.

Figure 1:
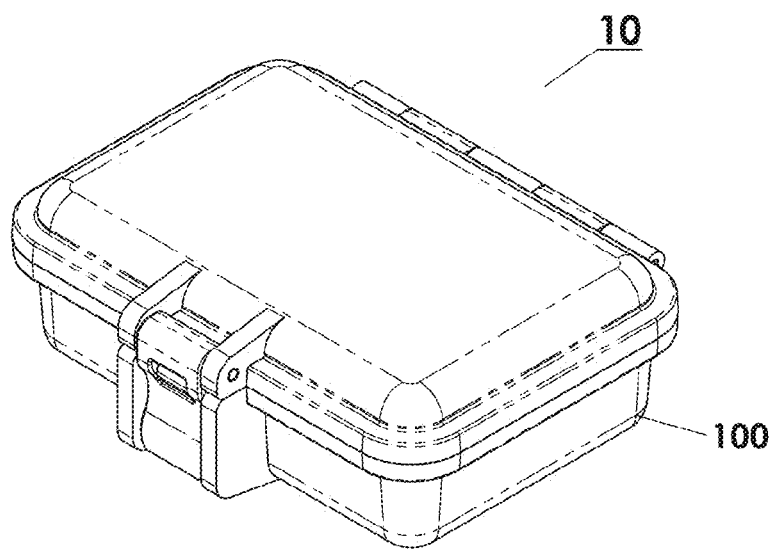
FIG. 1 depicts an isometric view of one embodiment of a nested box assembly in the closed position.
Figure 2:
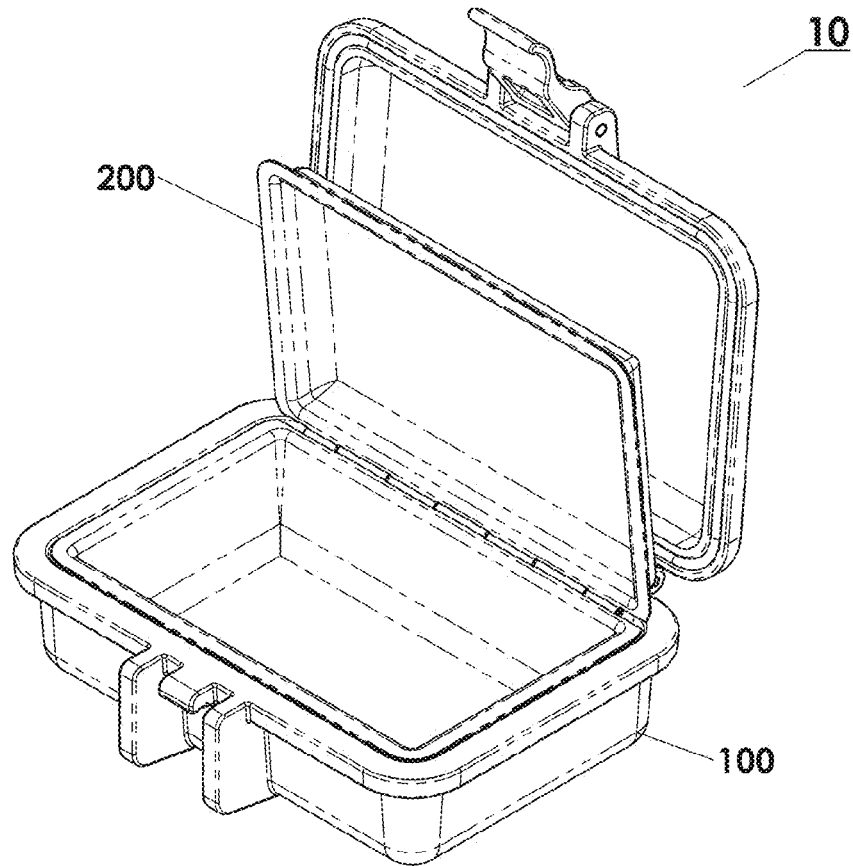
FIG. 2 depicts an isometric view of the nested box assembly of FIG. 1 in an exemplary open position.
Figure 3:
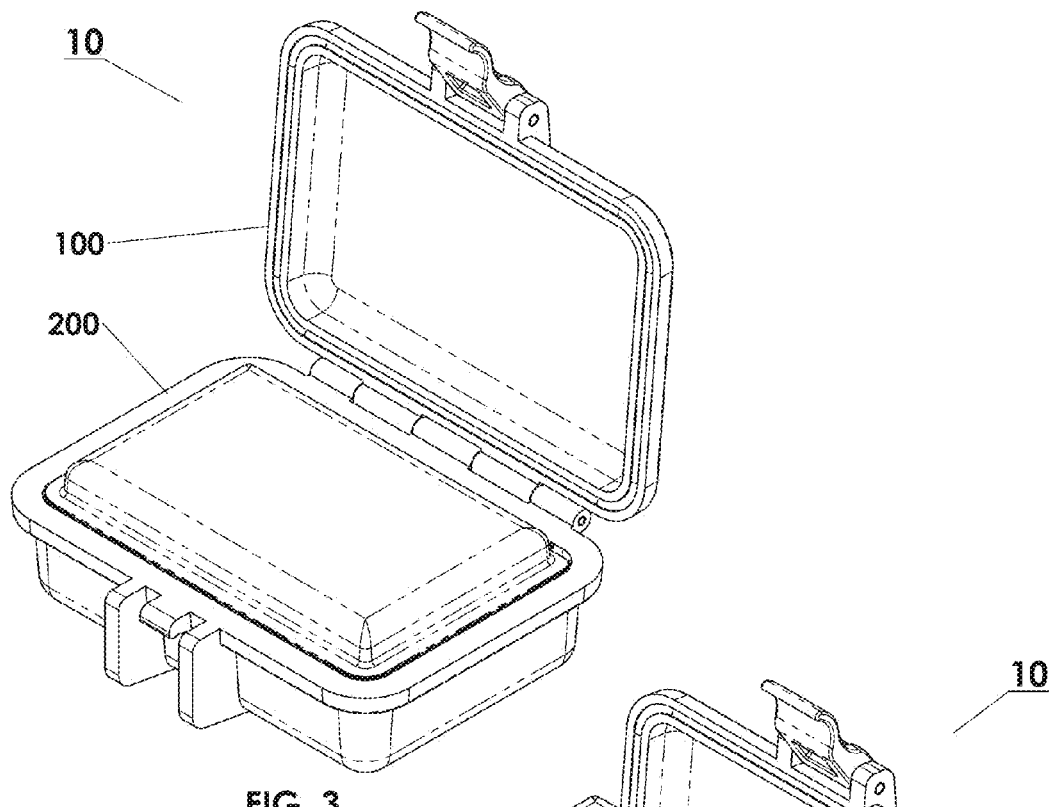
FIG. 3 depicts an isometric view of the nested box assembly of FIG. 1 with the inner box in a closed position.
Figure 4:
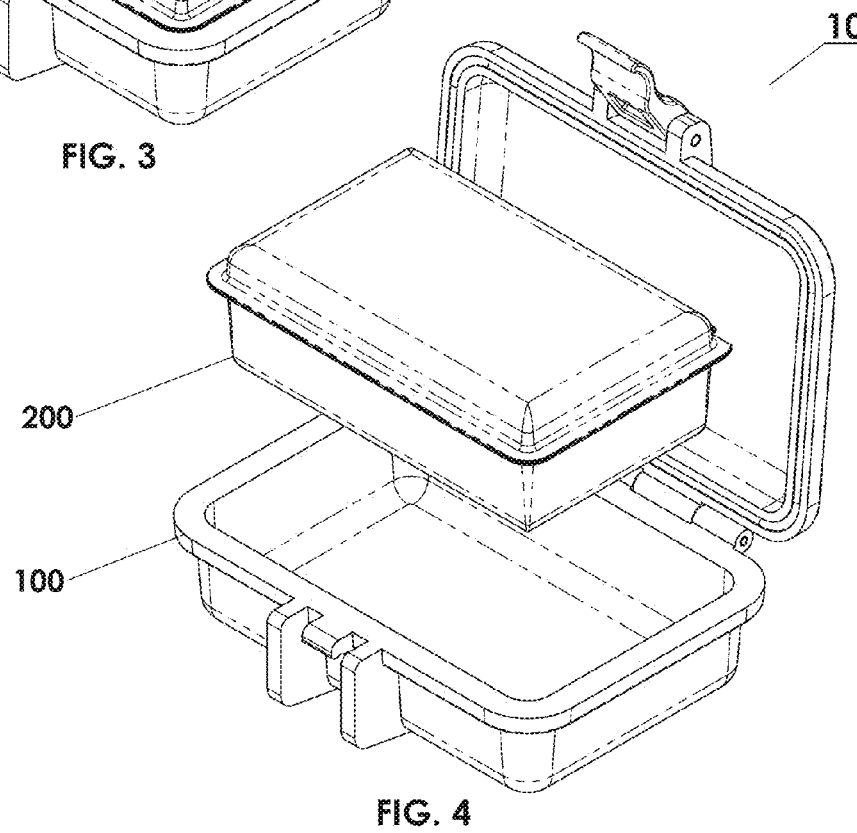
FIG. 4 depicts an isometric view of the nested box assembly of FIG. 1, highlighting the removability of the inner box.

FIGS. 1 through 9 depict various exemplary views of one embodiment of a nested box assembly 10, including in an open (FIG. 3) and closed (FIG. 5) condition. The nested box assembly 10 may include an inner box 200 and an outer box 100. The outer box 100 may be sized and configured such that the perimeter of the inner box 200 fits tightly within and inside the outer box 100 (as shown in FIG. 3), or the outer box may be significantly larger than the inner box (if desired). In the disclosed embodiment, the inner box 200 may be sized and configured to facilitate removal of the inner box 200 from the outer box 100 without difficulty, such as shown in FIG. 4.

Figure 5:
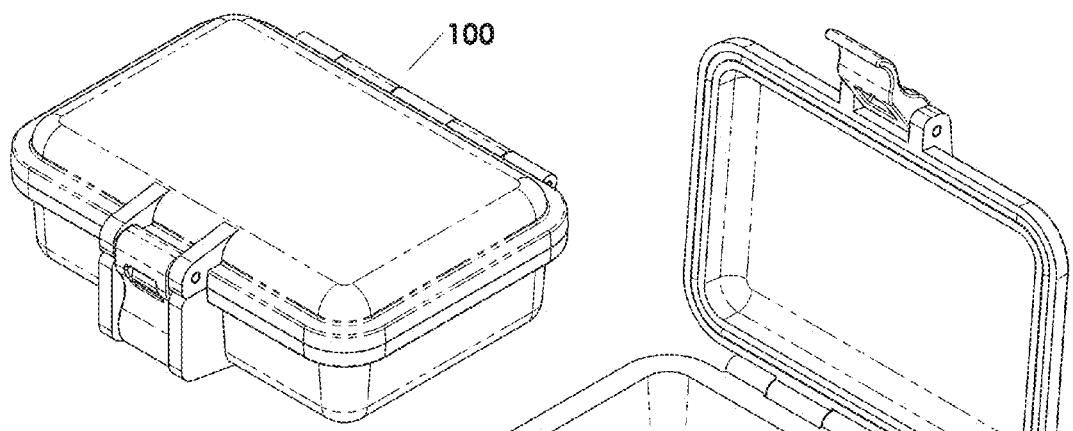
FIG. 5 depicts an isometric view of the outer box of FIG. 1 in a closed position.
Figure 6:
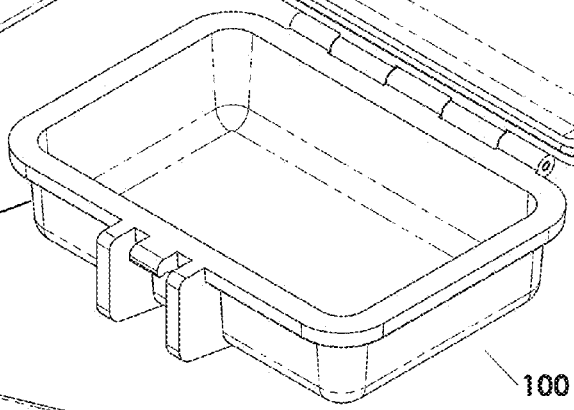
FIG. 6 depicts an isometric view of the outer box of FIG. 1 in an open position.
Figure 7:
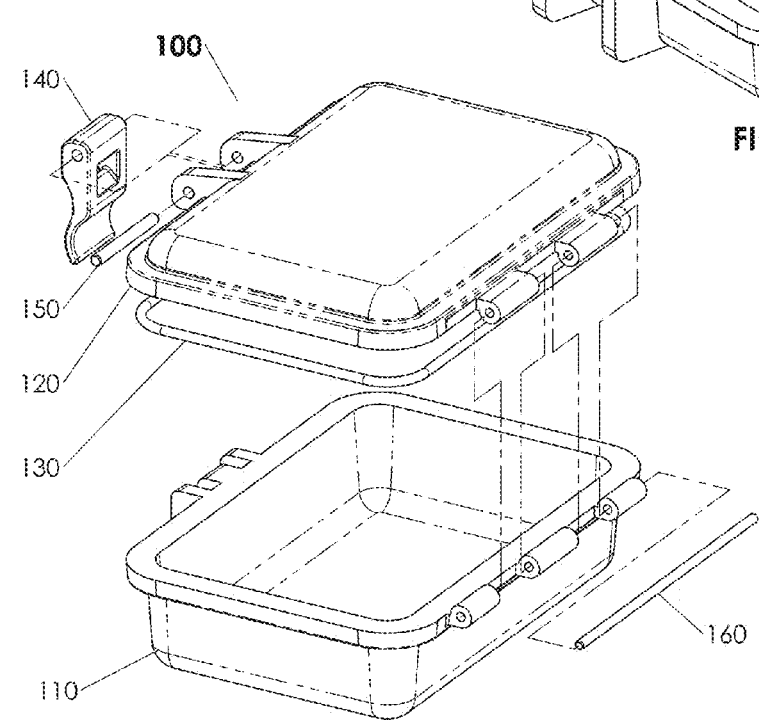
FIG. 7 depicts an exploded isometric view of the outer box of FIG. 1.

FIGS. 5 and 6 depict various isometric views of one embodiment of an outer box 100, in open (FIG. 6) and closed (FIG. 5) positions. The outer box 100 may include an outer bottom container 110, an outer box lid 120, an O-ring 130 or other type of seal, a latch mechanism 140, a latch pin 150 and an outer lid hinge pin 160, as best shown in FIG. 7. In addition, the outer box may also be used independently or in a nested configuration. It should also be understood that the seal can comprise a variety of shapes and configurations, including circular, non-circular, oblong, rounded, squared, triangular, elongated, and or other geometric and/or irregular shapes, cross-sections and/or thicknesses. In addition, the seal may comprise multiple independent seals or a plurality of seals (i.e., two or more nested seals on a single container and/or independent seals on multiple independent containers sealing to a single box lid), if desired.

Figure 8:
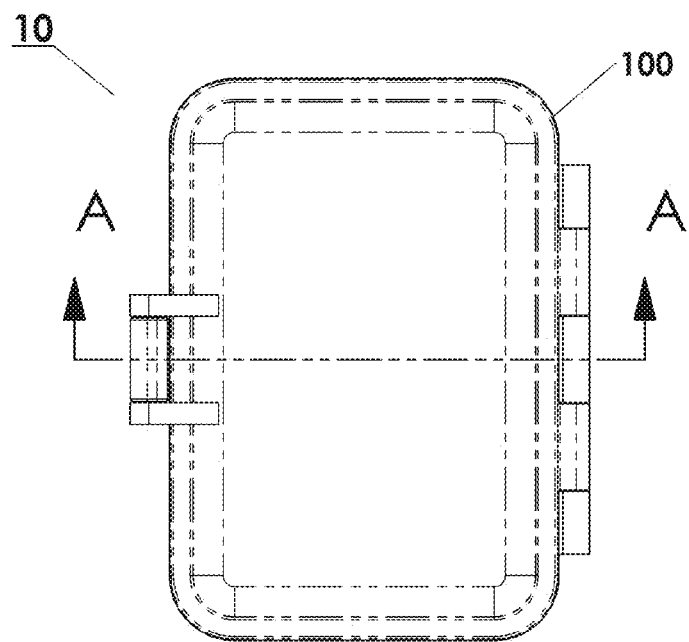
FIG. 8 depicts a top view of the nested box assembly of FIG. 1.
Figure 9:
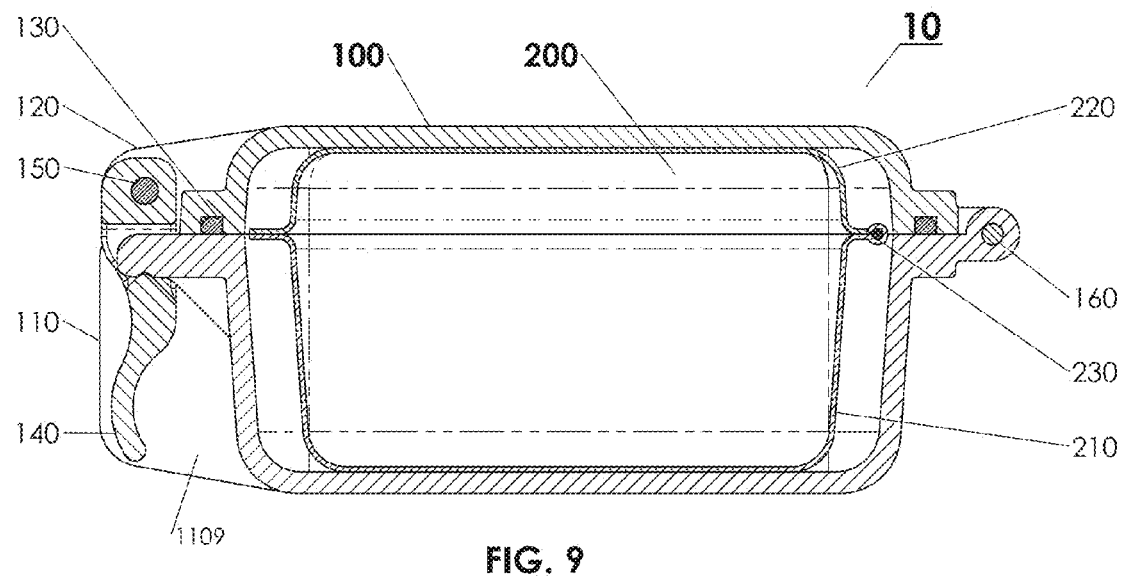
FIG. 9 depicts a side cross-sectional view of the nested box assembly of FIG. 1, taken along line A-A of FIG. 8.
Figure 10:
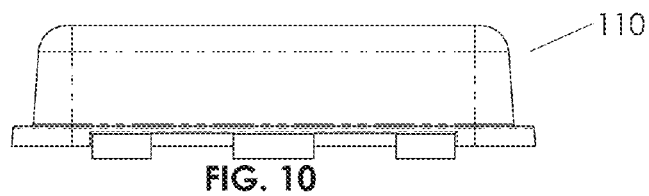
FIGS. 10-13 depict various exemplary views of an bottom half of the outer box of FIG. 1.
Figure 16:
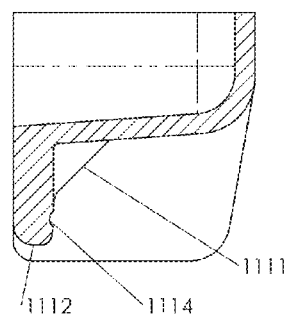
FIG. 16 depicts a magnified view of exemplary strengthening ribs of the outer box bottom container, taken along line B-B of FIG. 11.
Figure 43:
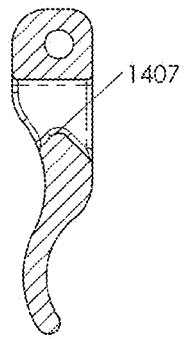
FIG. 43 depicts a cross-sectional side view of the latch of FIG. 42, taken along line H-H.

FIG. 9 depicts a side cross-sectional view of the nested box assembly (i.e., inner and outer boxes) taken along line A-A of FIG. 8. In this view, the inner container 200 is nested and fully contained within the outer container 100. The outer lid 120 of the outer container 100 is attached to the outer bottom portion 110 by the outer hinge pin 160. An O-ring 130 is shown in the groove in the outer lid 120, which can be compressed and sealed against the outer bottom portion 120 when the outer lid 120 is closed, desirably providing a dustless, water-tight seal to protect the inner container from contaminants. To provide a secure seal for the outer container, a latch 140 or other securement feature can be provided that in the disclosed embodiment is attached to the outer lid 120 by a latch pin 150 and locks in place when a male tab radius 1407 (see, for example, FIG. 43) of the latch 140 engages or otherwise locks into a latch lock recess 1114 (see FIG. 16) of locking tab 1112 (see FIG. 11) on the outer bottom portion 110. To prevent accidental unlatching and/or opening of the outer container 100 in a "floor-impact" situation, the latch 140 can be shielded and/or protected on both sides of the latch 140 by integral walls 1109 and 1110 on the outer bottom container 110, which desirably extend beyond the latch 140 when secured. The inner container 200 comprises an inner bottom portion 210 and an inner lid 220, which can be attached together at a hinge by an inner hinge pin 230.

While in the disclosed embodiment the inner and outer boxes are shown having congruent and parallel seams (i.e., both the inner and outer boxes open along a common plane), alternative embodiments could include non-parallel and/or non-congruent seams for the inner and outer boxes, if desired. In addition, in various embodiments features (not shown) for manipulating and/or lifting the inner box from the outer box could be used, such as projections, handles and/or bails.

Figure 11:
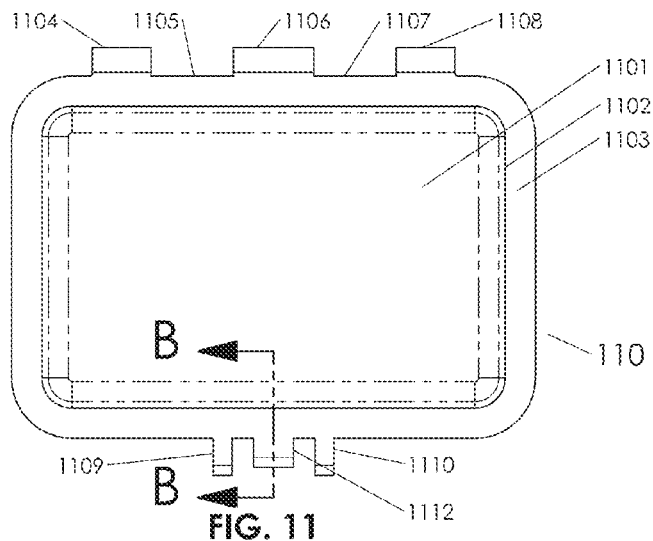
Figure 14:
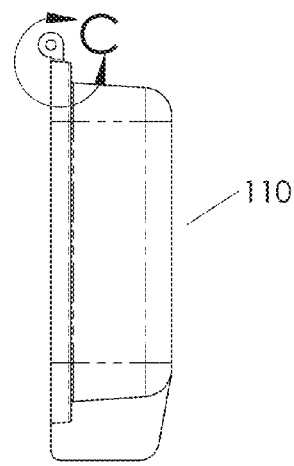
FIG. 14 depicts a side view of the outer box bottom container of FIG. 11.
Figure 12:
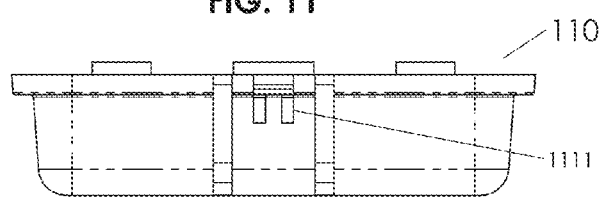
Figure 15:
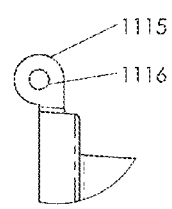
FIG. 15 depicts a magnified view of the hinge aperture of the outer box bottom container, taken along line C of FIG. 14.
Figure 13:
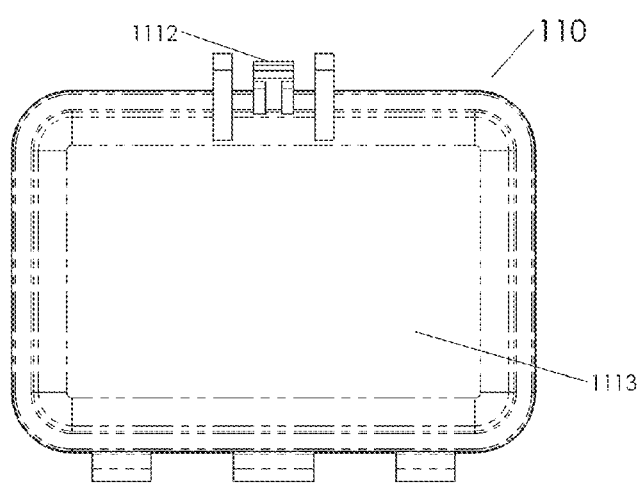
Figure 17:
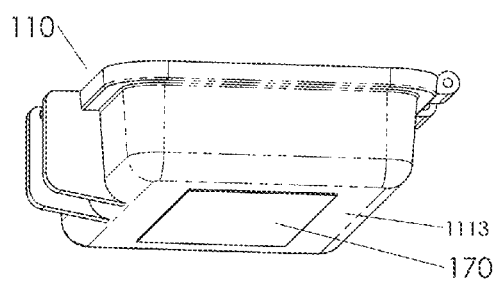
FIGS. 17-18 depict various isometric views of an alternative embodiment of an outer box with an adhesive bottom container.
Figure 93A:
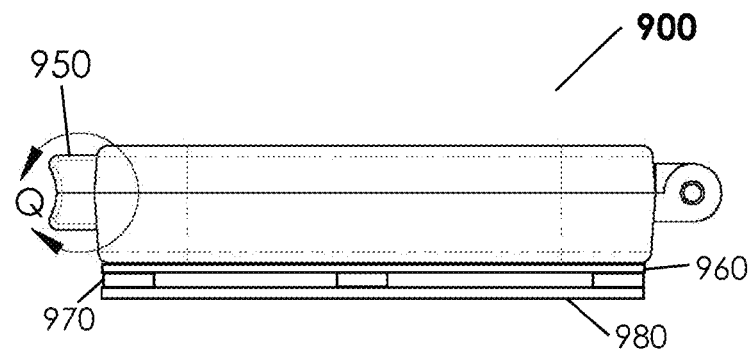
FIG. 93A depicts a side view of the nested pacemaker box assembly of FIG. 92.
Figure 93B:
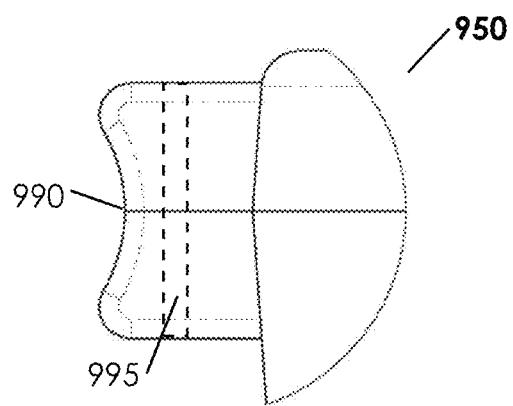
FIG. 93B depicts a magnified view of the magnetic latch mechanism on the nested pacemaker box assembly of FIG. 93A, taken along line Q.
Figure 94:
FIG. 94 depicts an isometric view of the nested pacemaker box assembly of FIG. 90.

FIGS. 10 through 13 depict various exemplary views of one embodiment of an outer box bottom container 110. As best seen in FIG. 11, the outer box bottom container 110 can include a recessed cavity that is desirably sized and configured to fit or otherwise accommodate the outer perimeter of one or more inner boxes 200. The recessed cavity includes an outer planar bottom surface 1113 (see FIG. 17); an inner planar surface 1101; an inner wall periphery 1102; and an O-ring sealing surface 1103. In the disclosed embodiment, the outer box bottom container 110 may be opened and/or locked using a hinge and latch mechanism or other similar feature. The hinge and latch mechanism can include male hinge portions 1104, 1106 and 1108; female hinge portions 1105 and 1107; integral walls 1109 and 1110; and locking tab 1112, and may also include strengthening ribs or other features (see FIGS. 12 and 16) for additional strength and structural support, which may be useful during a variety of conditions, including where "high force" latching or locking is desired (i.e., if dropped on the floor and/or disturbed during transport, etc). Various types of hinges may be contemplated, such as continuous hinges, butt hinges, barrel hinges, flush hinges, spring loaded hinges, double-action spring hinges, concealed hinges, and/or a combination thereof. Also, various types of latches may be used, such as slam latches, rotary latches, locking latches, adjustable latches, hooks, rotating locks, snapped, screws and/or sliding pins or magnetic latches (see FIGS. 93A and 93B) and/or any combinations thereof.

In various embodiments, the outer box (and/or the inner box, if desired) can include a spring loaded (not shown) or other mechanism (i.e., a detent, coil or spring mechanism) that desirably biases the outer and/or inner box lids to a closed condition. For example, the outer box lid may have a "catch" or other feature that allows the lid to stay open during use, but that causes the lid to close if the outer box is struck, disturbed or otherwise knocked over and/or onto the floor. For instance, a pendulum-type switch or other arrangement (i.e., an accelerometer or force transducer) could be provided that releases (and closes) the open lid when undesired contact with the outer box occurs, thereby closing the box and preventing the box contents from damage and/or contamination. In a similar manner, the inner box could include such a feature, in which the closing of the outer box could also impel closing of the inner box lid by direct contact between the lids or other features, with the inner box lid locking into place when closure of the outer box was completed.

Figure 18:
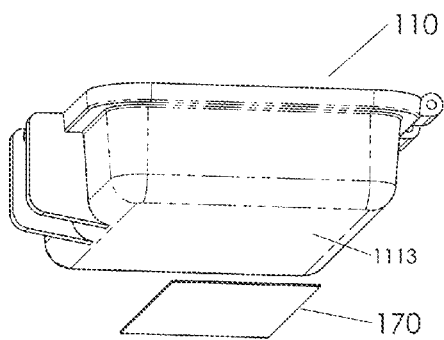
Figure 19:
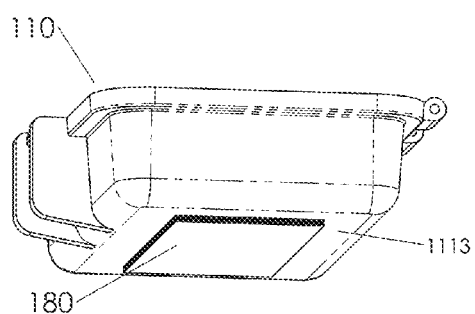
FIGS. 19-20 depict various isometric views of an alternative embodiment of an outer box with a hook and loop assembly (i.e., Velcro)
Figure 20:
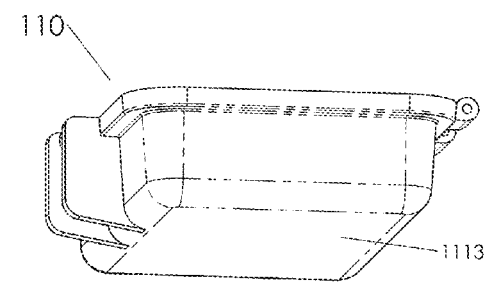
Figure 20:
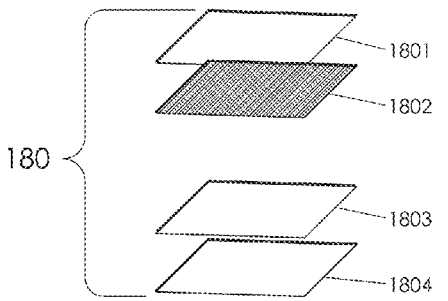
Figure 21:
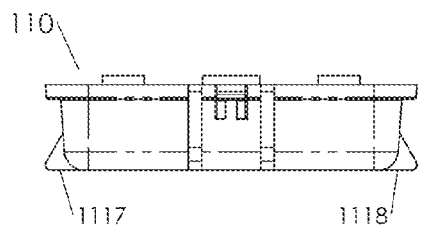
FIGS. 21-28 depict various exemplary views of another alternative embodiment of an outer box with strap rung supports.
Figure 22:
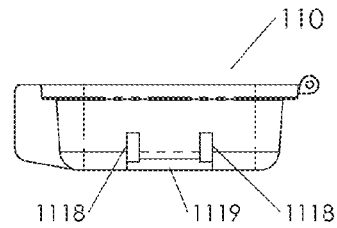
Figure 23:
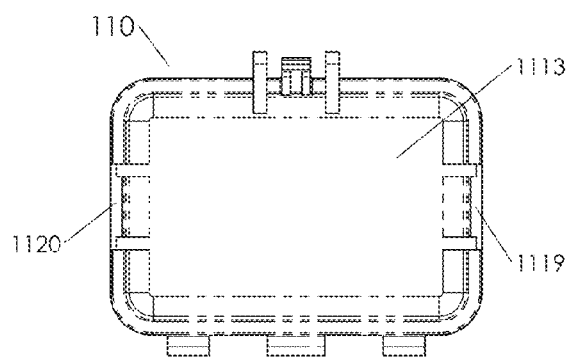
Figure 24:
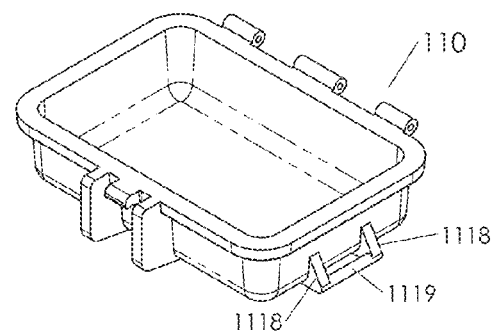
Figure 25:
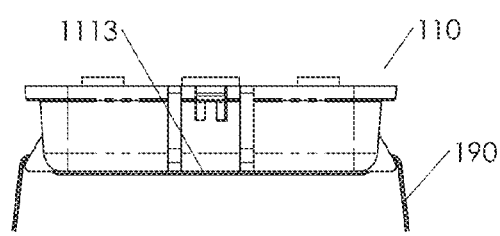
Figure 26:
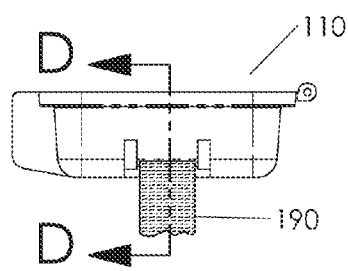
Figure 27:
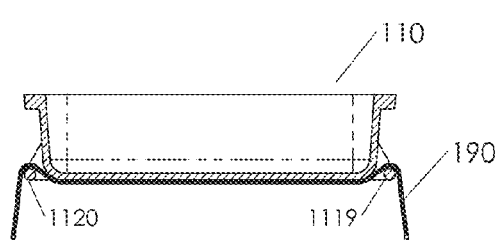
Figure 28:
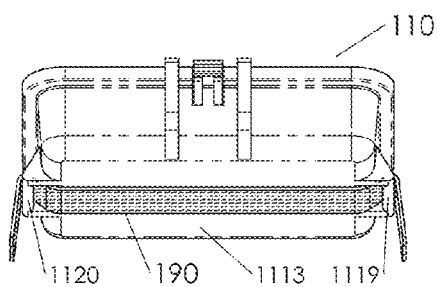
Figure 92:
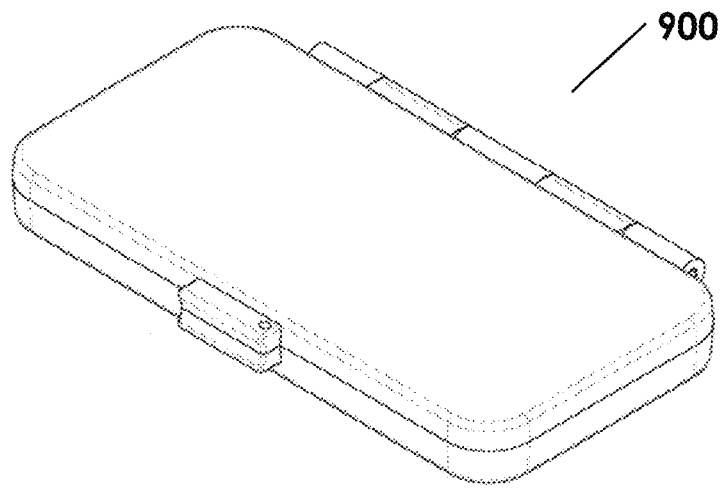
FIG. 92 depicts an isometric view of one embodiment of a nested pacemaker box assembly with a magnetic bottom surface.

In various embodiments, the outer planar bottom surface 1113 of the outer box bottom container 110 may include various connection, attachment securement and/or movement inhibiting components to desirably assist in securing the nested box assembly in a desired location and/or prevent accidental movement and/or falling from an area in which it is placed. These attachment components could include a variety of different systems, including the incorporation of an adhesive film layer 170 (see FIGS. 17 and 18), a portion of a hook and loop mechanism—i.e., Velcro (see FIGS. 19 and 20), various arrangements of strap rung supports 1117 and 1118 (see FIGS. 21-28), various types of magnetic components (see FIGS. 92, 93A and 93B), textured materials (not shown), rubberized materials (not shown) and/or any combinations thereof. If desired, the various attachment components may be permanently fixed onto the nested box assembly or may be removable (either directly removable from the box or as part of a modular attachment to the box). In various embodiments, the surgeon may wish to place the various attachment components in-situ (or may desirably select an attachment system from a plurality of different types of systems available in a kit form), and/or in a desired position on the nested box assembly. In the case of a magnetic attachment system, the magnetic components may alternatively be attached to the bottom of the inner box (not shown), with the magnetic field passing through the bottom material of the outer box and desirably anchoring the entire nested box in a manner to that similarly described.

For example, the outer planar bottom surface 1113 of the outer box bottom container 110 and/or the inner box bottom container 2109 might incorporate an adhesive film layer 170. The adhesive film 170 may include various types of adhesives known in the art, such as double-sided tape, pressure-sensitive tape, standard adhesives and/or a combination thereof. Alternatively, strap rung supports 1117 and 1118 or other connection features may be integrated (see FIGS. 17 and 18) into the outer box bottom container 110, where a security strap 190 or other securement feature may be threaded through the strap rung supports 1117 and 1118 to be adjustably tightened onto the area at which the nested box assembly is desirably positioned. In the various disclosed embodiments, it may be desirable that the securement or attachment features incorporated into the outer and/or inner boxes not significantly interfere with opening of the outer box and/or accessing of the inner box contents, unless such interfering features are desired by the surgeon or other operator for some reason.

FIGS. 29 through 33 depict various exemplary views of one embodiment of an outer box lid 120. As best seen in FIG. 30, the outer box lid 120 includes an upper planar lid surface 1201; an inner wall periphery 1202; a planar edge 1203; and an O-ring channel 1207. The 0-ring channel 1207 may be designed or configured to accept a standard O-ring size (or similar sealing feature known in the art) or may be a custom size. The O-ring channel 1207 desirably allows an O-ring to be inserted into the channel for sealing of the inner box when the upper lid is closed (with the O-ring optionally removable). In various embodiments, a removable O-ring can facilitate cleaning and/or sterilizing of the box, if desired. In various alternative embodiments, the top surface of the outer box lid 120 may include one or more recessed areas (not shown) in the upper lid planar surface 1201, if desired.

In various embodiments, the outer box lid 120 may be designed with an externally-located hinge mechanism, which may include male hinge portions 1204 and 1206; female hinge portion 1205 and latch hinge supports 1208 and 1209. Of course, virtually any type of hinge and latch mechanisms may be used as described herein and as known in the art, including internal hinges and/or hinge less designs as described herein, if desired. In various preferred embodiments, the outer box lid is connected so as to allow the outer box lid to completely rotate away from the inner box, thereby allowing free access to the inner box as desired.

In at least one exemplary embodiment, the outer and inner box lids may be linked in some manner, such as by a catch, hook or other feature, which facilitates simultaneous opening of the inner lid at the same time as the outer lid when they are opened by a user. Desirably, this arrangement would be "user selectable," in that the outer and inner lids would normally not be linked together unless desired by the user. For example, the outer lid could include a user-selectable switch or lever (not shown) which, when pressed by the user, would engage the inner lid to the outer lid, thereby opening the inner lid when the outer lid was opened. However, because the outer and inner lids were not normally linked in this manner, if the nested box were to fall to the floor and the outer lid broken or otherwise displaced from the outer box, the various impact forces would desirably not be transmitted directly to the inner lid, allowing the inner box to remain in a closed and sealed manner for "recovery" and usage of the inner box contents by the operating room personnel. In addition, the linkage can also be designed to disengage the "link" when the nested box exhibit various impact forces when falling to the floor.

In various embodiments, the outer box lid 120, the outer box bottom container 110, the inner box lid 220 and/or the inner box bottom container 210 can be designed using a variety of materials, including various types and/or combinations of plastics, metals and/or ceramics. The component materials may further contain additional composite additives and/or applied surface layers, such as hydrophobic/hydrophilic coatings, frictionless/non-stick coatings (i.e., Teflon), corrosion resistive coatings, moisture and chemical barrier coatings, hemocompatible coatings, anti-hemorrhagic coatings, and/or various combinations thereof.

Figure 37:
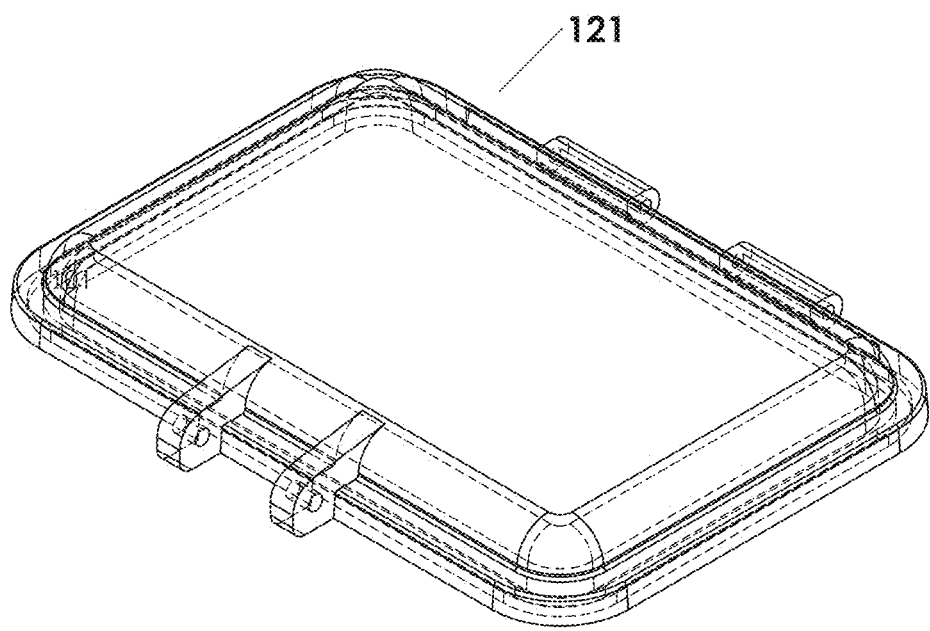
FIG. 37 depicts an isometric view of an alternative embodiment of a transparent outer box lid.
Figure 38:
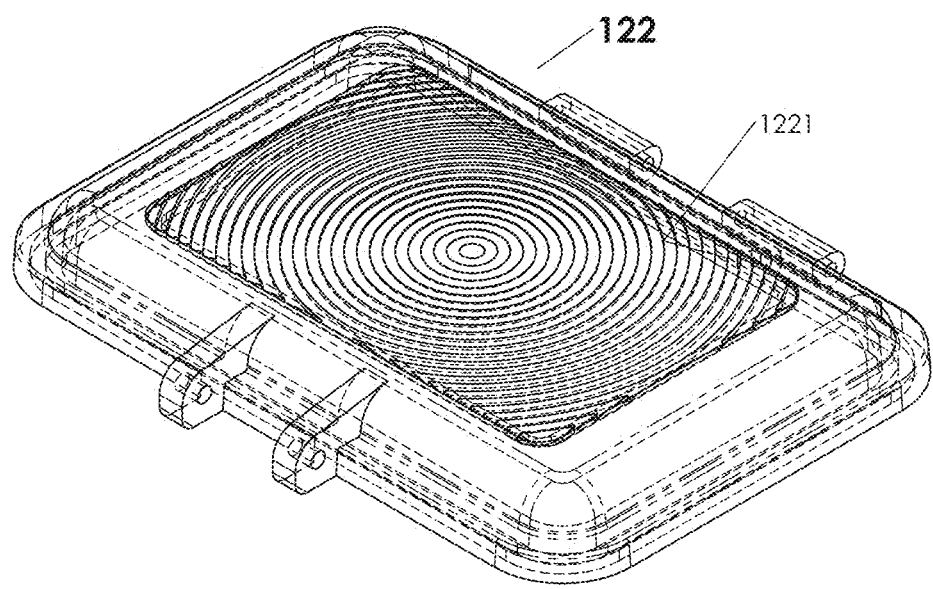
FIG. 38 depicts an isometric view of an alternative embodiment of a transparent outer box lid with a magnifying lens.
Figure 39:
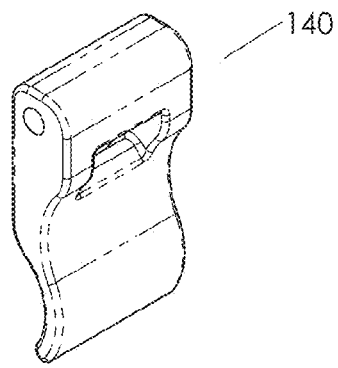
FIG. 39-42 depict various exemplary views of one embodiment of a latch assembly.
Figure 40:
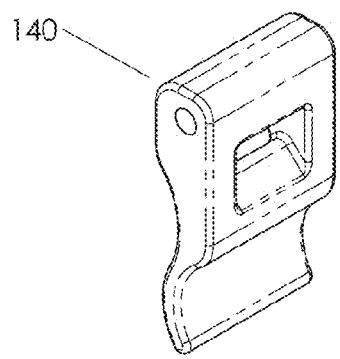
Figure 41:
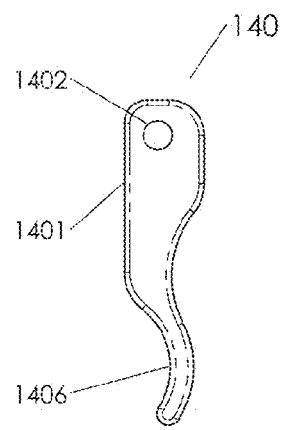
Figure 42:
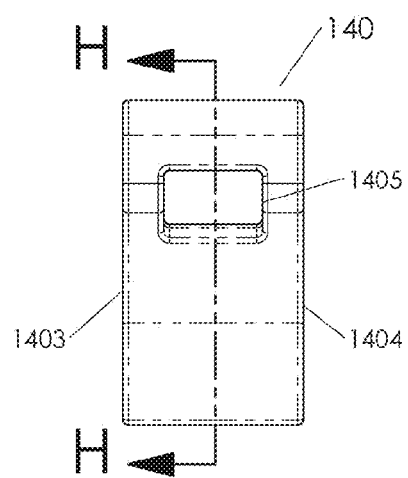
Figure 82:
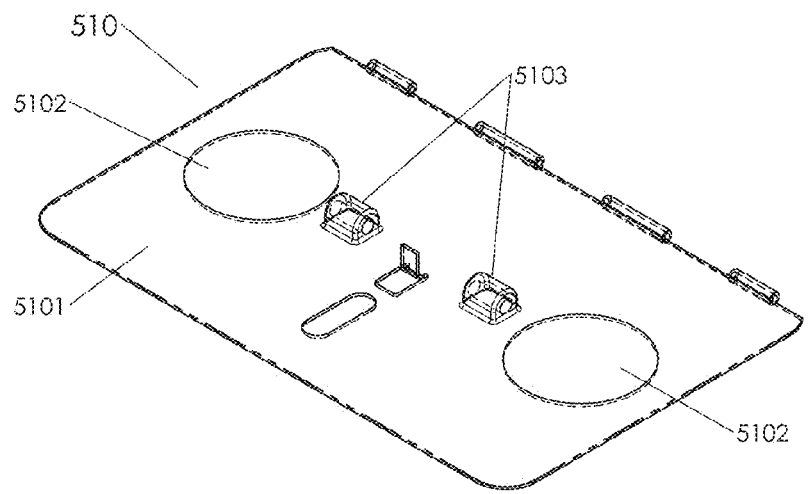
FIG. 82-83 depicts various exemplary views of the magnifying inner box lid of FIG. 80.
Figure 83:
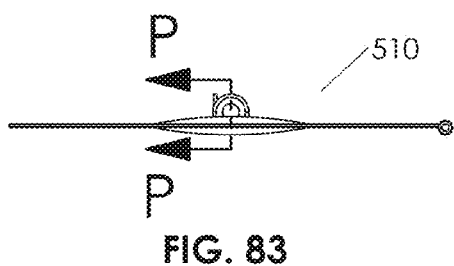
Figure 84:
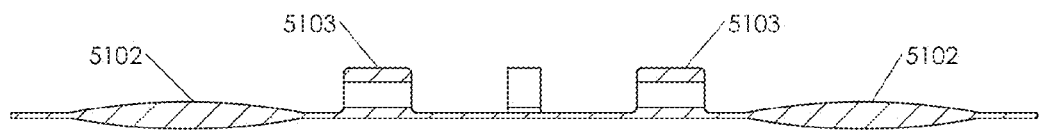
FIG. 84 depicts a side cross-sectional view of the magnifying inner box lid of FIG. 83, taken along line P-P.

In another exemplary embodiment, the outer box lid 120, the outer box bottom container 110, the inner box lid 220 and/or the inner box bottom container 210 may be formed from a transparent or opaque material. For example, it may be desirous for the outer box lid 120 to have a transparent outer box lid portion 121 (see FIG. 37) to allow viewing of the contents within the outer container 100 when the outer container is closed. In a similar manner, the inner box lid and/or entire box may be formed of transparent materials, and where both the outer and inner lids are transparent, the contents could be viewed and/or have their condition(s) verified without requiring opening of either box. In various additional embodiments, an optical enlargement and/or magnification panel 122 (see FIG. 38) may be added to the outer and/or inner box lid. If desired, one or more magnifying lenses 1221 and 5102 (see FIGS. 38 and 82) may be optionally added to the outer box lid 122 and/or inner box lid 220 as an integrated or removable features. The magnifying lens 1221 and 5102 may be Fresnel type lenses or other types of lenses, and it should be understood that the magnifying lens could be constructed in a variety of shapes and/or configurations, including as a single standard magnifying type lens, comprising of a single or double radius, or multiple magnifying lenses of various powers of magnification (i.e., differing types of lenses on the inner and outer box lids, which may work together to magnify the contents in a manner similar to telescopic optics, if desired). Also, the magnifying lenses 1221 and 5102 may be sized and configured to accommodate virtually any desired viewing capability known in the optical art.

Figure 44:
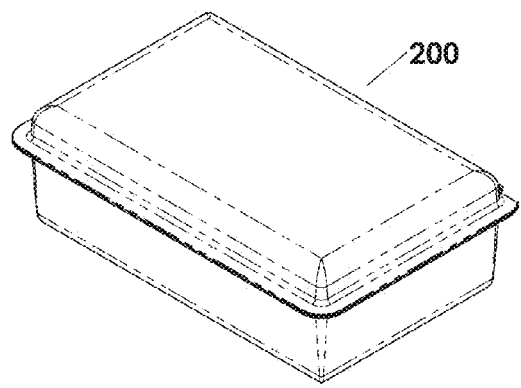
FIGS. 44-45 depict isometric views of one embodiment of an inner box in closed and open positions.
Figure 45:
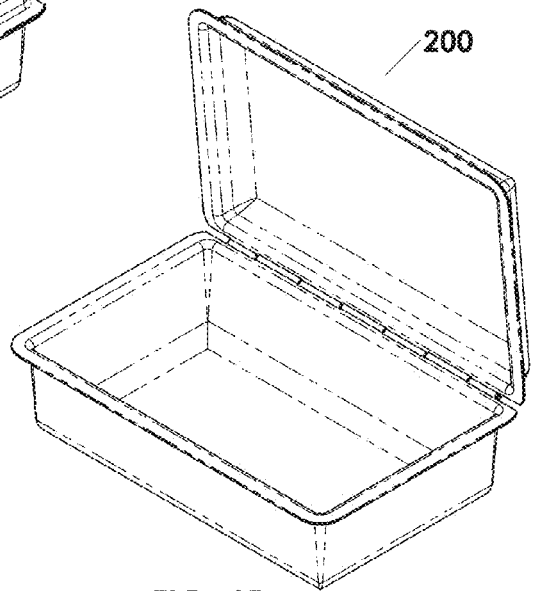
Figure 46:
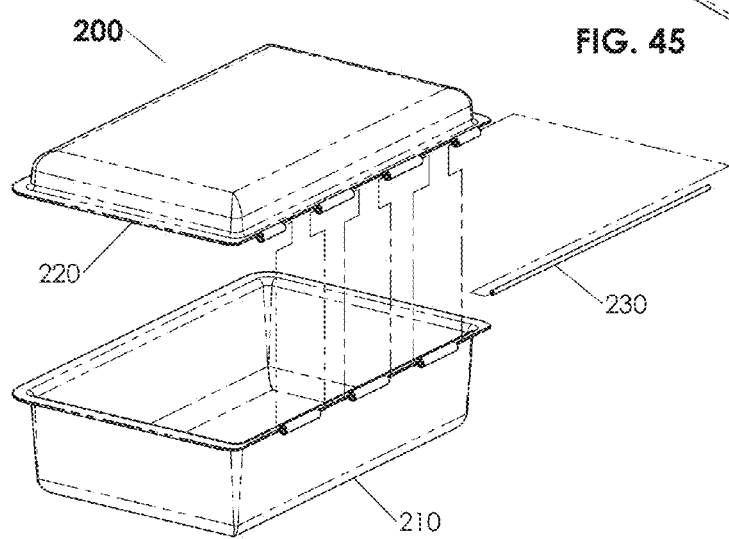
FIG. 46 depicts an exploded isometric view of one embodiment of the hinge assembly of the inner box of FIG. 44.
Figure 47:
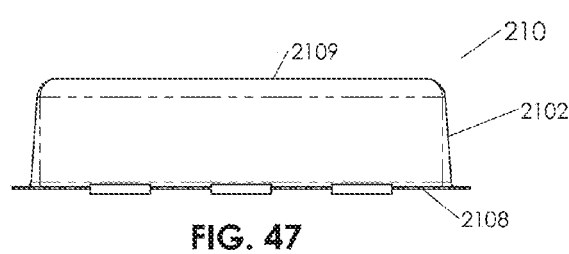
FIGS. 47-52 depict various exemplary views of one embodiment of an inner box bottom container.
Figure 53:
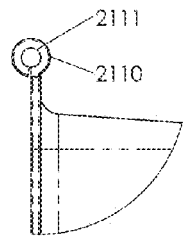
FIG. 53 depicts an enlarged view of the hinge aperture of the inner box bottom portion of FIG. 52, taken along line I.
Figure 48:
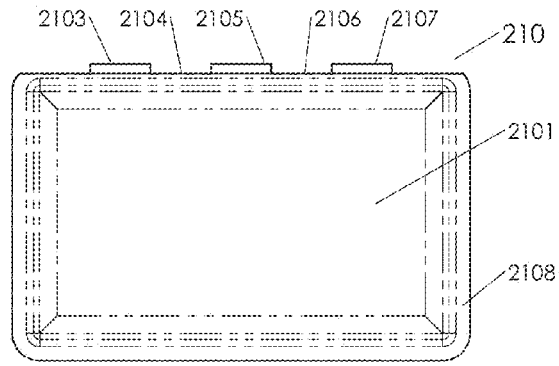
Figure 52:
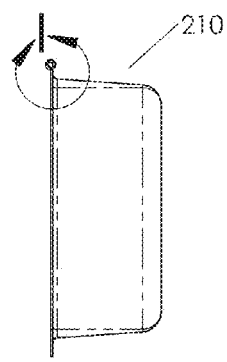
Figure 49:
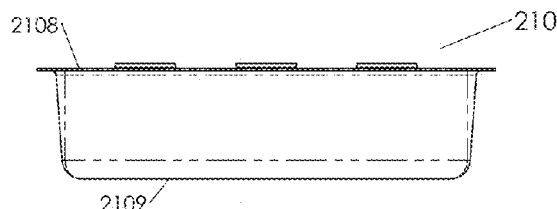
Figure 50:
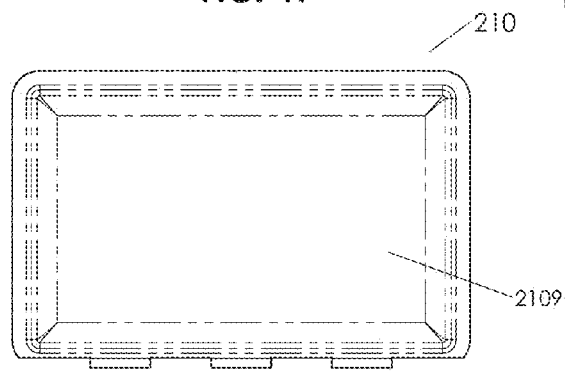
Figure 51:
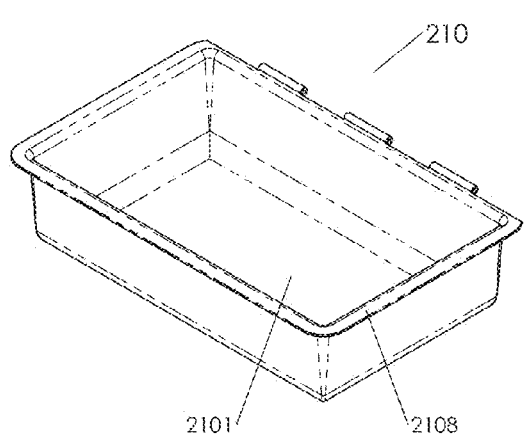
Figure 64:
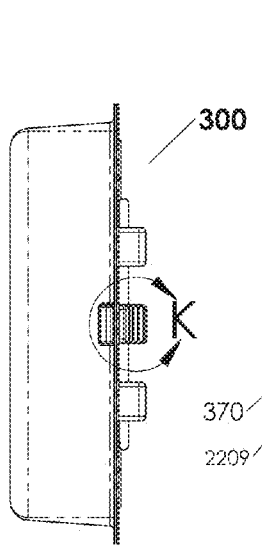
FIGS. 64-66 depict various exemplary views of the handle locking mechanism of FIG. 61.
Figure 65:
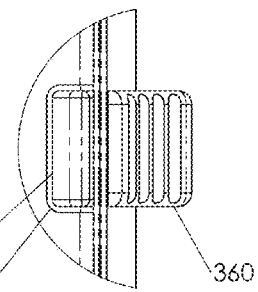
Figure 66:
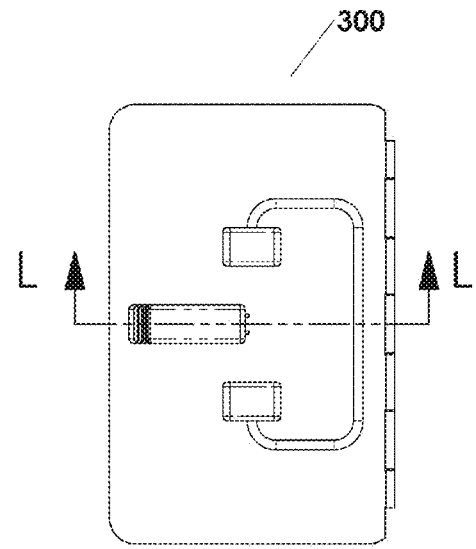

FIGS. 44 and 45 depict isometric views of one exemplary embodiment of an inner box 200 in an open (FIG. 44) and closed (FIG. 45) position. It should be understood that a variety of similar design features and considerations, and various combinations thereof, as described in conjunction with the outer box 100 may also be applied to various of the design features of the inner box (which may include similar, dissimilar and/or overlapping design features incorporated into one or both of the outer and inner boxes of a nested box arrangement), which is contemplated as described herein.

Figure 67:
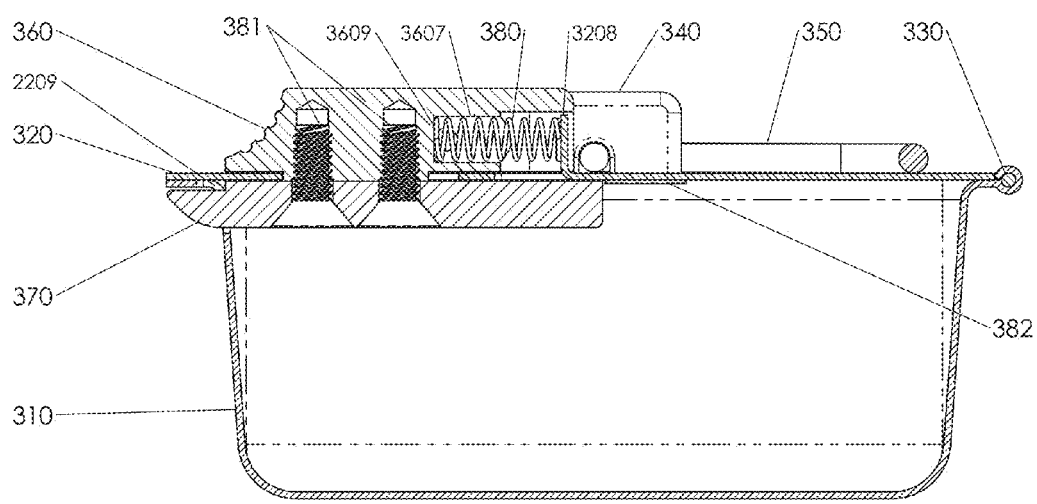
FIG. 67 depicts a cross-sectional side view of the handle locking mechanism of FIG. 66, taken along lines L-L of FIG. 66.
Figure 68:
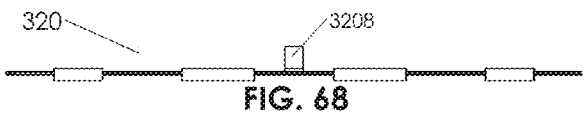
FIGS. 68-70 depict various exemplary views of the male and female hinges of the inner box lid of FIG. 67.

FIGS. 61 through 79 depict another alternative embodiment of an inner box 300, incorporating a "spring-loaded" latch type system. As best seen in the exploded view of FIG. 63 and cross-sectional view of FIG. 67, the inner box 300 includes an inner bottom portion 310 with a latch opening 2209; a latch lid 320; a latched hinge pin 330; a pair of handle retainers 340; a handle 350; a latch slider 360; a latch 370; a latch spring 380; various latch slider screws 381 and various latch handle retainer screws 382. The spring loaded latch system of this embodiment desirably allows the latch 370 to be secured in a locked or "engaged" position by operation of the latch spring 380 that is abutting the lid spring tab 3208 (see FIG. 67), with the spring 380 applying a biasing spring force against the spring pressure surface 3609 of the latch slider 360. The embodiment may be particularly useful where the outer box lid is capable of automatic closure during a fall, as the closure of the outer box lid can impel the inner box lid to close and latch shut, thereby securing the inner box contents against damage and/or contamination, even if the outer box lid is damaged and/or separates from the outer box bottom as a consequence of the fall.

In this embodiment, the latch spring 380 is desirably confined within the latch spring hole 3607 of the latch slider 360. The latch slider 360 is attached to the latch 370 with the latch slider screws 381. The latch 370 is shown in place in the latch opening 2209 of the latched inner bottom portion 310. Also shown is the handle 340 held in the openings of the handle retainers 340 which are attached to the latch lid 320 by the latch handle retainer screws 382. The latched hinge pin 330 is shown in place in the hinge components of the latch lid 320 and the inner bottom portion 310, linking the lid to the bottom portion yet allowing relative rotation of the lid. It is understood that the latching mechanism could be constructed in a variety of configurations including, but not limited to, hooks, rotating locks, "snap-fit" type mechanisms, screwed and/or interrupted pin mechanisms and/or sliding pins.

Figure 69:
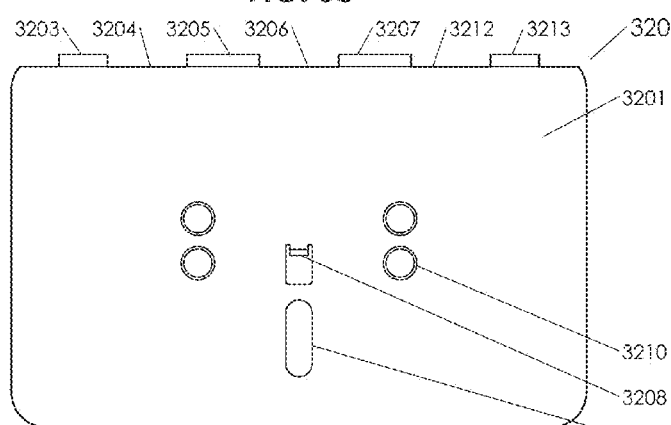
Figures 70, 71:
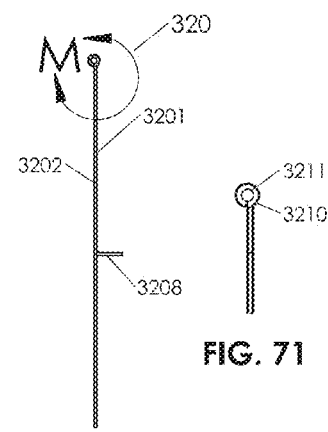
FIG. 71 depicts an enlarged view of the hinge aperture of the inner box lid of FIG. 70, taken along line M.

FIG. 69 is a top plan view of the latch lid 320 of the latch inner container 300, showing the lid spring tab 3208; male hinge portions 3203, 3205, 3207 and 3213; female hinge portions 3204, 3206 and 3212; latch handle retainer screws 382 and the female oval latch slider opening 3209 that desirably accepts the male oval guide 3604 of the latch slider 360. In this embodiment, the length of the female oval latch slider opening 3209 is desirably longer than the length of the male oval guide 3604 of the latch slider 360 to limit the movement of the latch 370.

Figure 72:
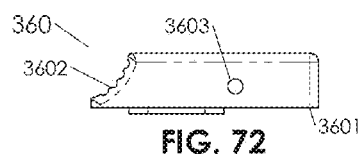
FIGS. 72-79 depict various exemplary views of one embodiment of a latch slider.

FIG. 72 is a side view of the latch slider 360 showing the ridged surface 3602 which can be provided to improve the grip of a finger and/or thumb of the user when moving the latch slider 360 against the spring. In this embodiment, the inner box could desirably be opened and/or closed using a single hand of the surgeon or associated operating room personnel, such as by grasping the handle 350 with the fingers of a single hand and operating the latch slider 360 with the thumb of the same hand. This could allow the lid to be opened and the contents accessed by a single individual, where desired. This embodiment can also include a drainage through-hole 3603, which can facilitate cleaning and/or sterilization of the latch spring 380 and/or the latch slider planar surface 3601. If desired.

Figure 73:
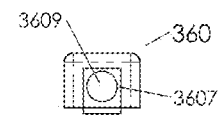
Figure 74:
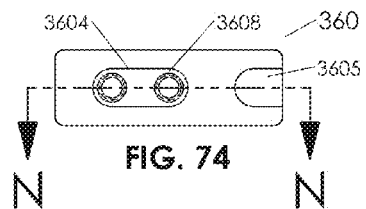
Figure 76:
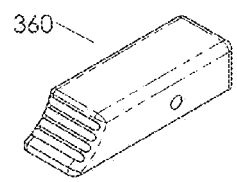
Figure 75:
Figure 77:
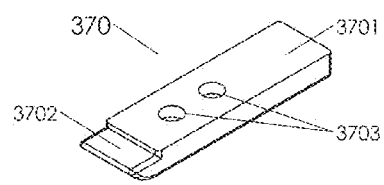
Figure 78:
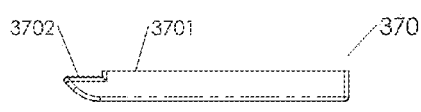
Figure 79:
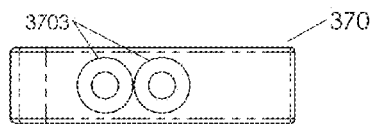
Figure 80:
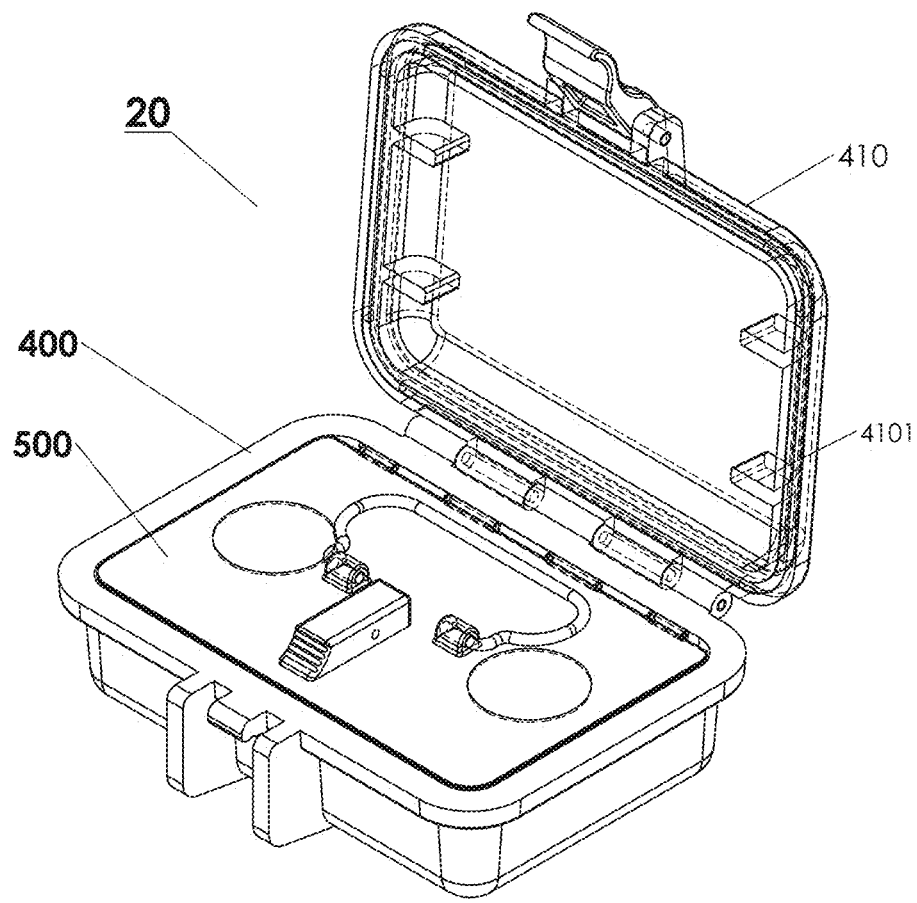
FIGS. 80-81 depict various isometric views of an alternative embodiment of a nested box assembly with a magnifying inner box lid.
Figure 81:
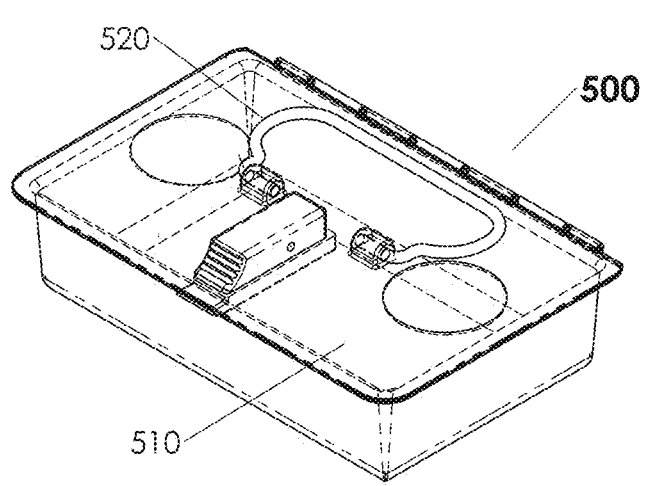

FIGS. 73 through 76 depict one embodiment of a latch slider 360. FIG. 73 is an end view of the latch slider 360, which highlights the latch spring hole 3607 and the spring pressure surface 3609. FIG. 74 is a bottom view of the latch slider 360 and contains the section line N-N. Also shown are the male oval guide 3604; latch slider screw holes 3608 and lid spring tab clearance channel 3605. FIG. 75 is a sectional view along line N-N of FIG. 74 and shows the optional drainage through-hole 3603; the spring pressure surface 3609; the latch spring hole 3607 and the lid spring tab clearance channel 3605.

Figures 85, 86:
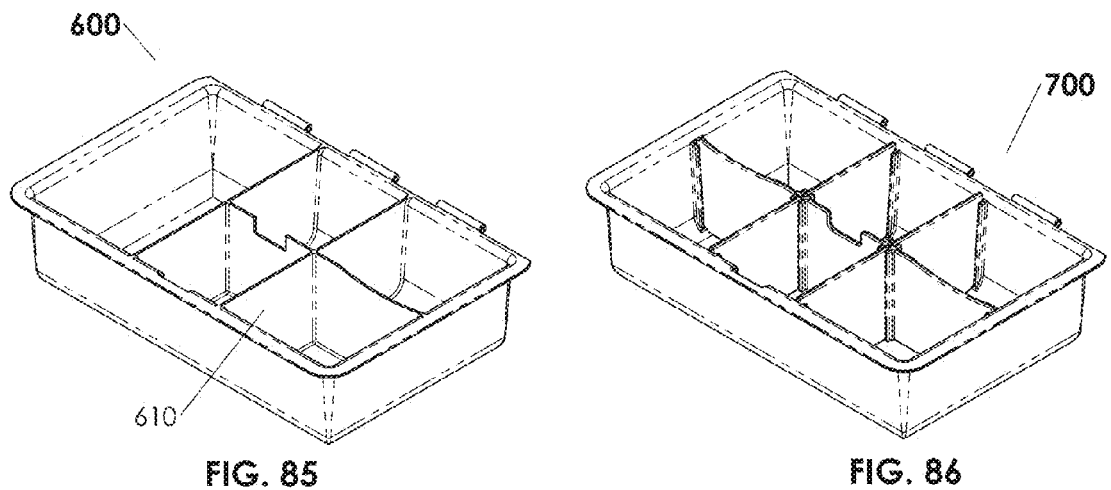
FIGS. 85-86 depict isometric views of an alternative embodiment of an adjustable compartmentalized inner box bottom container.
Figure 87:
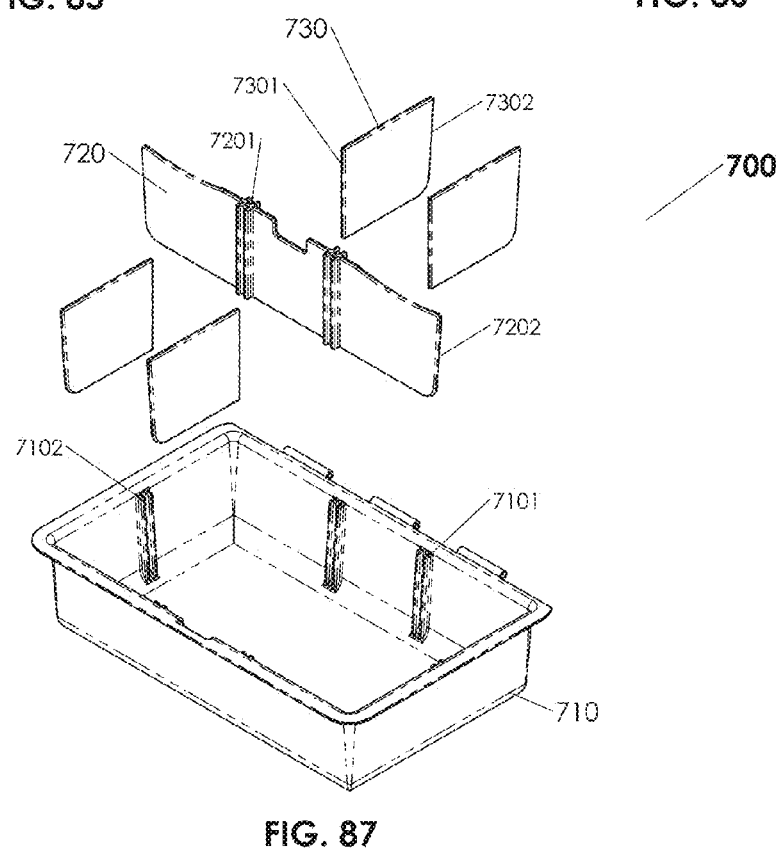
FIG. 87 depicts an isometric exploded view of the adjustable compartmentalized inner box bottom container of FIG. 86.

In another alternative embodiment, such as depicted in FIGS. 85 through 89, the outer box bottom container and/or the inner box bottom container may be user-customizable, which may include the provisions of a variety of integrated and/or adjustable separators and/or compartments. For example, FIG. 85 depicts an isometric view of one embodiment of a compartmentalized inner bottom portion 600 having integrated walls 610 that can be used to separate specimens held in the inner container. The number and size of each compartment within the inner box can be more or less than what is shown in the example of FIG. 85, as well as placed in any user defined configuration. In various alternative embodiments, the outer box bottom container and/or the inner box bottom container may include features that facilitate the placement of a variety of removable and/or adjustable walls 720 as shown in FIGS. 86 and 87. The number and size of each partition can of course be more or less than what is shown in the FIG. 86.

FIG. 87 depicts an exploded isometric view of another embodiment incorporating removable and/or adjustable compartments in the inner bottom portion 700, consisting of the adjustable inner bottom portion 710 and adjustable partitions 720 and 730. The adjustable inner bottom portion 710 contains channels 7101 and 7102 that accept partitions 720 and 730 at edges 7202 and 7302. Partition 720 contains channels 7201 which accept edge 7301 of the partition 730.

Figure 88:
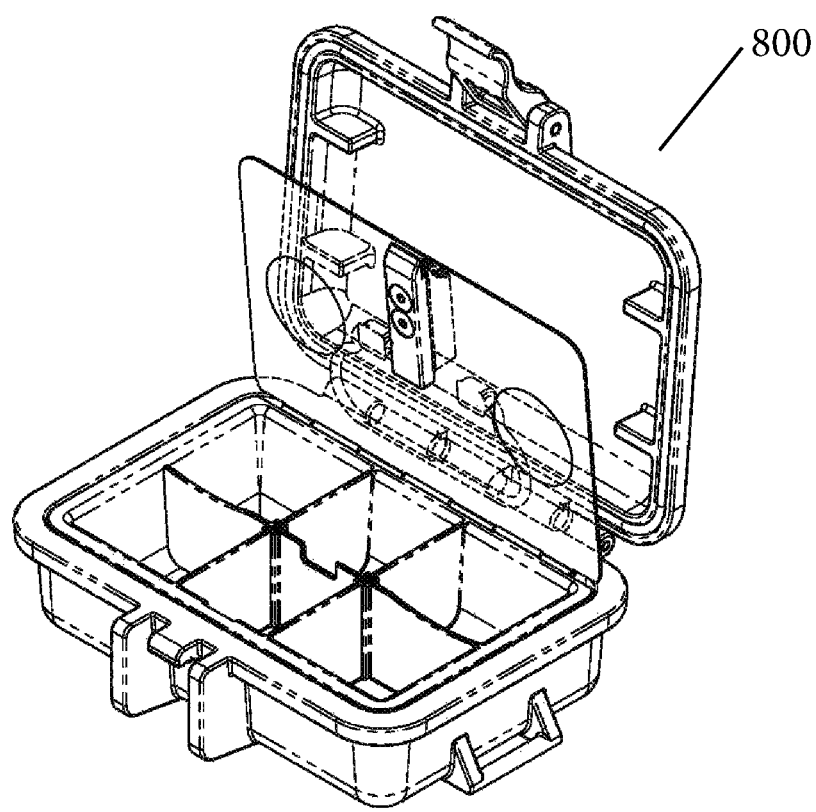
FIGS. 88-89 depict various exemplary views of a nested box assembly with an adjustable compartmentalized inner box.
Figure 89:
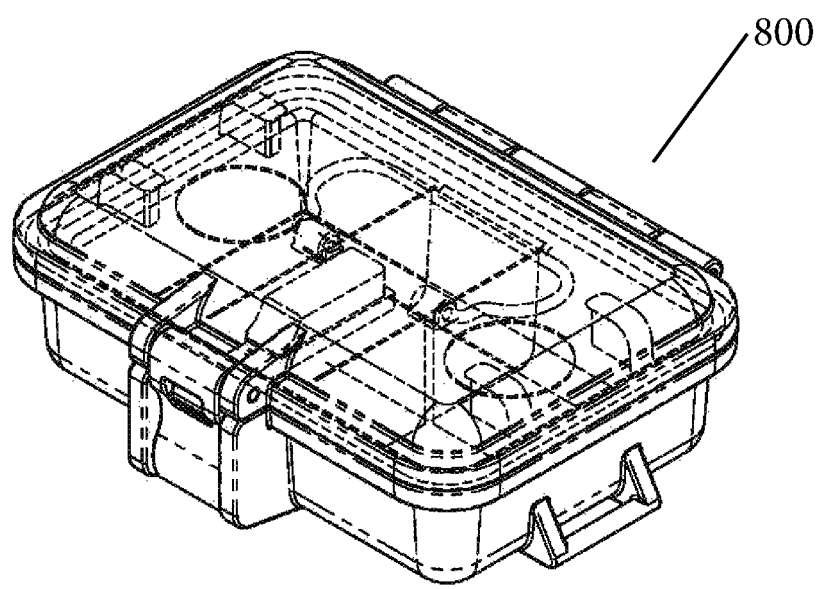
Figure 90:
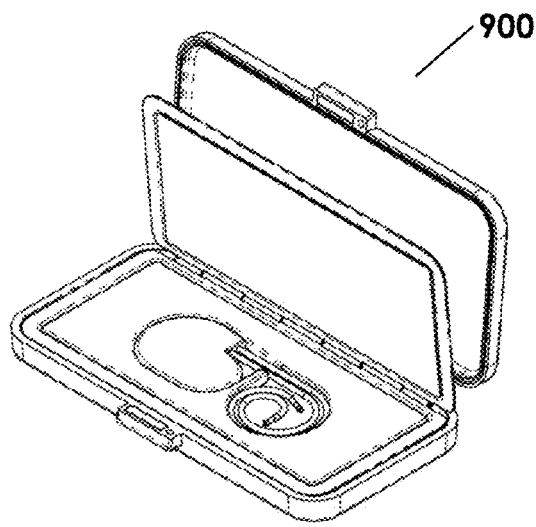
FIG. 90 depicts an isometric view of one embodiment of a nested pacemaker box assembly.
Figure 91:
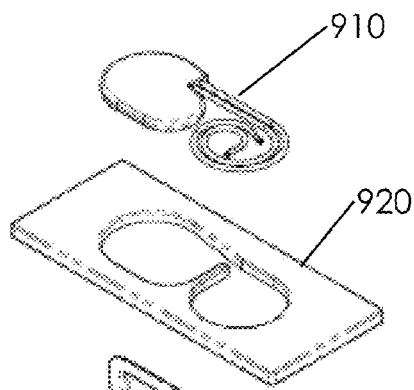
FIG. 91 depicts an exploded isometric view of the nested pacemaker box assembly of FIG. 90.
Figure 91:
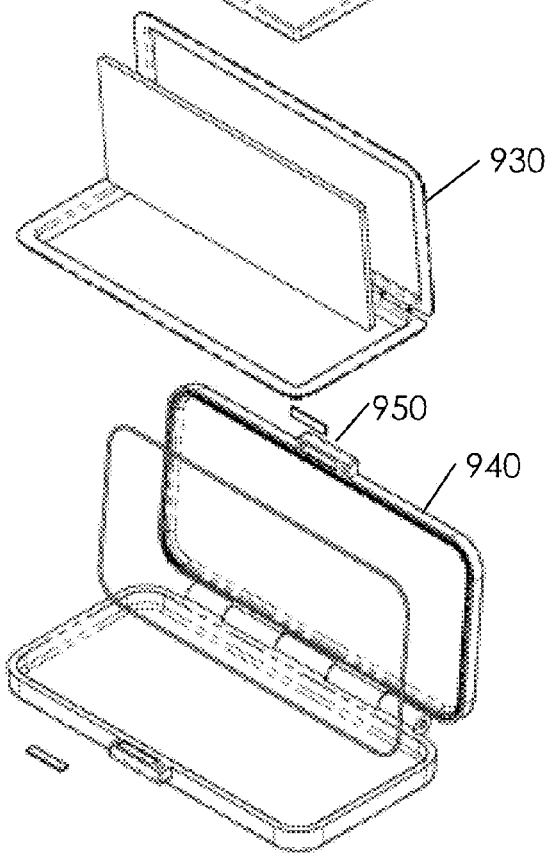

FIGS. 88 and 89 depict isometric views of another exemplary embodiment of a compartmentalized nested box design 800 in both an open (FIG. 88) or closed (FIG. 89) configuration. In the depicted embodiment, the inner box is shown with a flat lid, although a removable and/or spring loaded lid could be provided if desired, including variations of such shapes and sizes as described herein.

Figure 99:
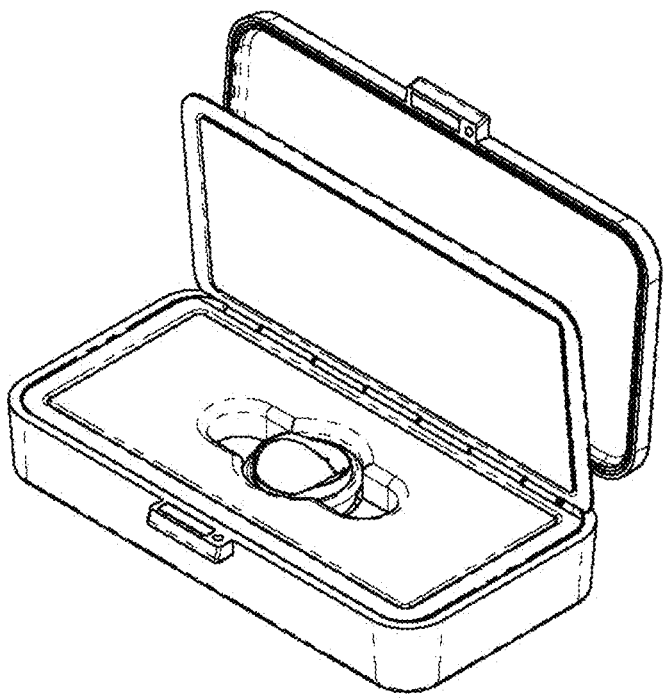
FIG. 99 depicts an isometric view of one embodiment of a nested heart valve box assembly.

In another alternate embodiment, such as shown in FIGS. 90 through 94, a nested box assembly may be customized to fit a desired size and/or configuration of virtually any specimen, tissue, device, implant and/or tool. For example, the nested box assembly may be custom-designed to fit a standard pacemaker 910, such as shown in FIG. 91 through 94, or a heart valve, such as shown in FIG. 99. The pacemaker nested box 900 may include a pacemaker 910, a mold cut-out and/or liner 920, an inner box 930 and an outer box 940. Alternatively, the custom designed nested boxes may come equipped with magnetic connections to secure the nested box during surgery and prevent the box from falling from the table. Such magnetic components may be placed at the outer box 940 bottom planar surface or between the two latch surfaces. For example, a plurality of magnetic components may be used on the outer box 940 and/or the inner box 930. At least one magnetic sheet, film or layer 960 may be placed on the bottom planar surface of the outer box 940 or the inner box 930. In addition, at least one magnet piece 970 may be desirably placed in selected locations below the magnetic sheet 960 that will be in contact with a skid proof magnetic drape 980. Furthermore, the locking or latching mechanism 950 may incorporate magnetic interfaces 990. The magnetic interface 990 may allow the alignment of a through-hole or aperture 995 that provides a visual cue for a tamper evident seal. Where it is desirable to secure the box to a non-ferrous, weakly ferrous and/or non-magnetic material (i.e., a plastic or wooden table or tray, or a highly austenitic stainless steel table), an auxiliary magnet and/or small portion of ferrous metal may be provided for placement under the non-ferrous material, which will subsequently be attracted to the magnetic surface of the box, desirably sandwiching the non-ferrous material therebetween.

Figure 95:
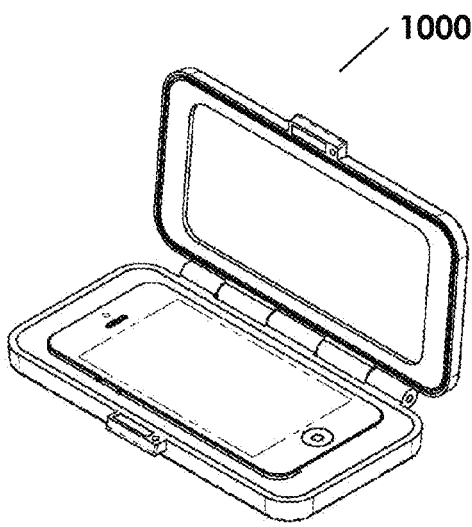
FIGS. 95-97 depict various isometric views of one embodiment of a mobile phone nested box assembly.
Figure 96:
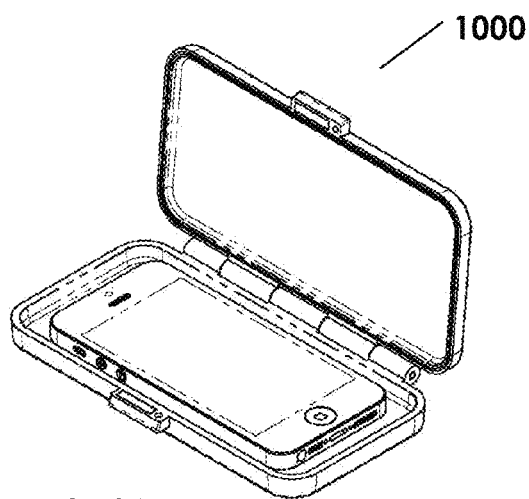
Figure 97:
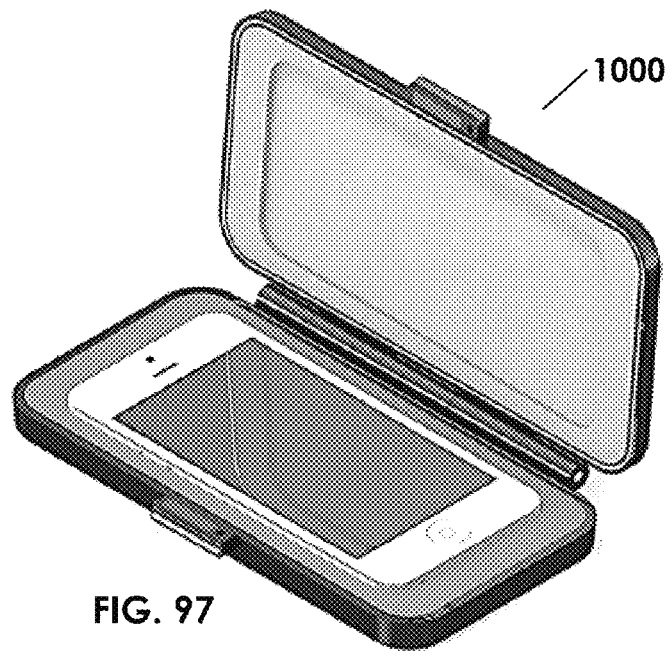

As previously described, the manufacturer may incorporate a variety of other features into the design of a single or nested box, such as predisposing the various box components for multiple uses after the intended single use of the single and/or nested box. Various designs could include features that facilitate secondary cleaning, sterilization and/or other decontamination procedures to be performed on the box and/or its component parts to allow a third party to reuse or recycle the box designs for completely different applications. For example, as best seen in FIGS. 95 through 97, the shape and dimensions of popular consumer electronics, such as cell phones, cameras, music players, tablets, and glasses, or for items used in outdoor environments such as first-aid kits, flashlights, and matches, may "match" (to various degrees) the shape and/or dimensions of an inner and/or outer protective box design of FIG. 94. The protective box manufacturer may design the protective box components so as to facilitate storage and/or protection of such third-party devices (after initial use in the surgical procedure), and in the depicted embodiment, the removal of the inner box allows a consumer to use the outer box for placement and fit of an iPhone®, which desirably keeps some or all of the "used" box components out of the waste stream, and can potentially provide a marketing and/or sales benefit as the original customers can keep the recycled box for their own use. In various alternative embodiments, the component parts of the inner and outer box (i.e., the various lids, bottoms and any inserts or partitions) might be capable of disassembly and the component portions capable of reassembly into different configurations, creating a final construct that differs from either or both of the original inner and/or outer box.

Figure 98:
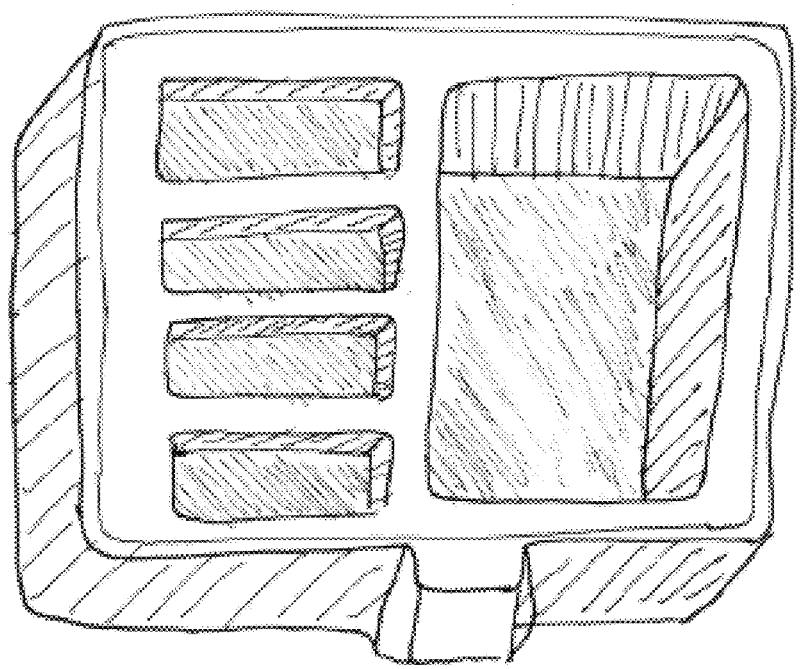
FIG. 98 depicts a top view of one embodiment of a custom compartmentalized nested box assembly.

FIG. 98 depicts another embodiment of a nested box that incorporates a plurality of customized compartment sizes, depths and/or shapes. In various embodiments, a customized and/or customizable inner box can be provided, with one or more compartments sized and configured for implants and/or surgical tools, while other compartments can be designed to accommodate tissue samples and/or grafts that may be removed and/or implanted during the surgical procedure. In this manner, the inner box could provide safe and secure holding and/or storage for various implants and/or materials employed during the surgical procedure. In a similar manner, one or more compartments within the inner box could be utilized for mixing and/or combining of tissues with other materials, such as bone morphogenic proteins, antibiotics, saline, etc.

The entire disclosure of each of the publications, patent documents, and other references referred to herein is incorporated herein by reference in its entirety for all purposes to the same extent as if each individual source were individually denoted as being incorporated by reference.

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

What is claimed:

1. A method of protecting one or more implantable surgical articles from contamination or damage prior to a surgical implantation procedure in a patient, comprising:
   placing the one or more implantable surgical articles within a first sealable enclosure and closing the first sealable enclosure, the first sealable enclosure including a substantially sterile interior and exterior;
   placing the first sealable enclosure completely within a second sealable enclosure and closing the second sealable enclosure to fully encapsulate the first sealable enclosure, the second sealable enclosure including a substantially sterile interior and exterior;
   placing the second sealable enclosure within a sterile field of a surgical procedure; and
   maintaining the second sealable enclosure in a closed condition until at least one of the one or more implantable surgical articles is to be utilized for direct implantation into the patient;
   wherein the first sealable enclosure has a first interior void, the first interior void bounded by a first lower surface, at least one first peripheral wall, a first closeable lid, and at least one modular partition sized and configured for placement within the first interior void of the first sealable enclosure, the modular partition dividing the first interior void into a plurality of compartments, the first closeable lid including an airtight seal capable of isolating the at least one implantable surgical article within the first interior void from a first environment external to the first sealable enclosure; and the second sealable enclosure having a second interior void, the second interior void bounded by a second lower surface, at least one second peripheral wall and a second closeable lid, the second closeable lid including an airtight seal capable of isolating the second interior void from a second environment external to the second sealable enclosure.

2. The method of claim 1, further comprising the step of attaching the second sealable enclosure to an object in the sterile field.

3. The method of claim 2, wherein an outer surface of the second sealable enclosure comprises a movement inhibiting component.

4. The method of claim 1, wherein damage to the second sealable enclosure does not compromise the substantially sterile interior of the first sealable enclosure.

5. The method of claim 1, wherein a flexible material is positioned between the first sealable enclosure and the second sealable enclosure.

6. The method of claim 1, further comprising a user operable linkage between the first closeable lid and the second closeable lid that selectively connects the first closeable lid to the second closeable lid.

7. The method of claim 1, wherein the second closeable lid is biased to a closed position.

8. The method of claim 7, wherein the second closeable lid is biased to a closed position and includes a locking feature which releaseably secures the second closeable lid in an open position.

9. The method of claim 1, wherein the first closeable lid is biased to a closed position and includes a locking feature which releaseably secures the first closeable lid in an open position.

10. The method of claim 1, wherein the first sealable enclosure is completely removable from the second sealable enclosure.

11. The method of claim 1, wherein both of the first and second closeable lids comprise a transparent material.

12. The method of claim 11, wherein at least one of the first and second closeable lids comprises a transparent material capable of optically magnifying the contents of the first or second sealable enclosures.

13. The method of claim 1, wherein the modular partition provides a watertight seal between the plurality of compartments.

14. The method of claim 1, wherein the first sealable enclosure comprises a disposable container and the second sealable enclosure comprises a reusable container.

15. The method of claim 1, wherein the at least one modular partition divides the first interior void into a plurality of different sized compartments.

16. A method of protecting an implantable surgical article from contamination or damage prior to a surgical implantation procedure in a patient while transferring the article from a first sterile environment through a non-sterile environment to a second sterile environment, comprising:
    placing the implantable surgical article within a first sealable enclosure and closing the first sealable enclosure, the first sealable enclosure including a substantially sterile interior and exterior;
    placing the first sealable enclosure completely within a second sealable enclosure and closing the second sealable enclosure to fully encapsulate the first sealable enclosure, the second sealable enclosure including a substantially sterile interior;
    transferring the second sealable enclosure from the first sterile environment through the non-sterile environment to a location proximate to the second sterile environment;
    opening the second sealable enclosure and removing the first sealable enclosure from the second sealable enclosure;
    placing the first sealable enclosure within the second sterile environment; and
    opening the first sealable enclosure;
    wherein the first sealable enclosure has a first interior void, the first interior void bounded by a first lower surface, at least one first peripheral wall, a first closeable lid, and at least one modular partition sized and configured for placement within the first interior void of the first sealable enclosure, the modular partition dividing the first interior void into a plurality of compartments, the first closeable lid including an airtight seal capable of isolating the at least one implantable surgical article within the first interior void from a first environment external to the first sealable enclosure; and the second sealable enclosure having a second interior void, the second interior void bounded by a second lower surface, at least one second peripheral wall and a second closeable lid, the second closeable lid including an airtight seal capable of isolating the second interior void from a second environment external to the second sealable enclosure.

17. The method of claim 16, wherein the first sealable enclosure is not directly connected to the second sealable enclosure.

18. The method of claim 16, wherein the first sealable enclosure is completely removable from the second sealable enclosure.

* * * * *